United States Patent
Furet et al.

(10) Patent No.: US 8,859,586 B2
(45) Date of Patent: Oct. 14, 2014

(54) CYCLOHEXYL ISOQUINOLINONE COMPOUNDS

(75) Inventors: Pascal Furet, Thann (FR); Vito Guagnano, Basel (CH); Philipp Holzer, Sissach (CH); Joerg Kallen, Basel (CH); Keiichi Masuya, Basel (CH); Stefan Stutz, Basel (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/127,159

(22) PCT Filed: Jun. 19, 2012

(86) PCT No.: PCT/EP2012/061691
§ 371 (c)(1),
(2), (4) Date: Dec. 17, 2013

(87) PCT Pub. No.: WO2012/175487
PCT Pub. Date: Dec. 27, 2012

(65) Prior Publication Data
US 2014/0275158 A1 Sep. 18, 2014

Related U.S. Application Data

(60) Provisional application No. 61/498,815, filed on Jun. 20, 2011.

(51) Int. Cl.
C07D 217/22 (2006.01)
A61K 31/47 (2006.01)
A61K 31/4725 (2006.01)
A61K 31/472 (2006.01)
C07D 405/08 (2006.01)
C07D 401/08 (2006.01)
C07D 217/24 (2006.01)

(52) U.S. Cl.
CPC .......... *C07D 217/24* (2013.01); *A61K 31/4725* (2013.01); *A61K 31/472* (2013.01); *C07D 405/08* (2013.01); *C07D 401/08* (2013.01)
USPC ......................................... 514/309; 546/141

(58) Field of Classification Search
None
See application file for complete search history.

(56) References Cited

U.S. PATENT DOCUMENTS 8,440,693 B2   5/2013   Berghausen et al.

FOREIGN PATENT DOCUMENTS

| WO | 2005117876 | 12/2005 |
| WO | 2008034039 | 3/2008 |
| WO | 2011076786 | 6/2011 |
| WO | 2012/175520 A1 | 12/2012 |
| WO | 2013/080141 A1 | 6/2013 |

OTHER PUBLICATIONS

Ivanov et al., Polyphosphoric acid-induced construction of quinazolinone skeleton from 1-(3,4-dimethoxyphenyl)-3-phenylurea and carboxylic acids. Heterocycles. May 12, 2006;68(7):1443-9.

*Primary Examiner* — Heidi Reese
(74) *Attorney, Agent, or Firm* — Scott W. Reid

(57) ABSTRACT

The invention relates to compounds of formula (I): as defined in the application. Such compounds are suitable for the treatment of a disorder or disease which is mediated by the activity of MDM2 and/or MDM4, or variants thereof.

15 Claims, No Drawings

CYCLOHEXYL ISOQUINOLINONE COMPOUNDS

The present invention relates to cyclohexyl isoquinolinone compounds capable of inhibiting the interaction between p53, or variants thereof, and MDM2 and/or MDM4, or variants thereof, respectively, especially binding to MDM2 and/or MDM4, or variants thereof, a process for the preparation of such compounds, pharmaceutical preparations comprising such compounds, uses and methods of use for such compounds in the treatment (including therapy and/or prophylaxis), and/or related subject matter as specified below. p53 refers to all genes and/or proteins encoded thereof with the names TP53, p53, TP73, p73, TP63, TP73L, p63. MDM2 refers to all genes and/or proteins encoded thereof with the names MDM2, Mdm2, HDM2, Hdm2. MDM4 refers to all genes and/or proteins encoded thereof with the names MDM4, Mdm4, HDM4, Hdm4, MDMX, MdmX, HDMX, HdmX.

Protein p53 is known as a tumor suppressor protein which helps to control cellular integrity and prevents the proliferation of permanently damaged cells by initiating, among other responses, growth arrest or apoptosis (controlled cell death). p53 mediates its effects in that it is a transcription factor capable of regulating a number of genes that regulate e.g. cell cycle and apoptosis. Thus, p53 is an important cell cycle inhibitor. These activities are tightly controlled by MDM2, an important negative regulator of the p53 tumor suppressor. "MDM2" (originally from the oncogene "murine double minute 2") refers both to the name of the gene as well as the protein encoded by that gene. MDM2 protein functions both as an E3 ubiquitin ligase that recognizes the N-terminal trans-activation domain (TAD) of the p53 tumor suppressor and thus mediates the ubiquitin-dependent degradation of p53, and as an inhibitor of p53 transcriptional activation.

The original mouse oncogene, which codes for the MDM2 protein, was originally cloned from a transformed mouse cell line. The human homologue of this protein was later identified and is sometimes also called HDM2 (for "human double minute 2"). Further supporting the role of MDM2 as an oncogene, several human tumor and proliferative disease types have been shown to have increased levels of MDM2, including inter alia soft tissue sarcomas, bone cancer, e.g. osteosarcomas, breast tumors, bladder cancer, Li-Fraumeni syndrome, brain tumor, rhabdomyosarcoma and adrenocortical carcinoma and the like. Another protein belonging to the MDM2 family is MDM4, also known as MDMX.

Dysregulation of the MDM2/p53 ratio, e.g. due to mutations, polymorphisms or molecular defects in the affected cells, can thus be found in many proliferative diseases. MDM2, in view of its mentioned effects, is capable to inhibit the activity of the tumor suppressor protein p53, thus leading to loss of p53's tumor suppressor activity and inhibiting regulatory mechanisms that impede cells from uncontrolled proliferation. As a consequence, uncontrolled proliferation can take place, leading to cancers such as tumors, leukemias or other proliferative diseases.

WO2008/034039 discloses tetrahydroisoquinoline compounds as ligands binding to the HDM2 protein. WO 03/095625 discloses benzodiazepine compounds that bind to HDM2 and interfere with its interaction with proteins such as p53.

There is a need for new drugs that are capable of interfering with the interaction between p53 and MDM2 or especially oncogenic variants thereof and that thus allow p53 to exert its beneficial effect against uncontrolled tumor growth, allowing it e.g. to accumulate, to arrest the cell cycle and/or to cause apoptosis of affected cells.

It has now been found that a novel class of cyclohexyl isoquinolinone compounds shows potent inhibition of the MDM2/p53 interaction (this term including in particular Hdm2/p53 interaction) and the corresponding compounds thus represent a novel type of compound that are useful in the treatment of a number of disorders, such as cancer. The invention relates therefore to these compounds as drugs as well as to the other inventive embodiments indicated herein.

The compounds of the invention also show inhibition of the MDM4/p53 interaction (this term including in particular Hdm4/p53 interaction).

Particularly interesting compounds of the invention herein are highly potent in the p53-Hdm2 inhibition (TR-FRET) assay described herein. Compounds of particular interest possess favourable pharmacokinetic properties. They provide an optimum balance of several pharmaceutically advantageous properties. They should be non-toxic and demonstrate few side-effects. Furthermore, the ideal drug candidate will exist in a physical form that is stable, non-hygroscopic and easily formulated.

The invention therefore provides a compound of the formula (I):

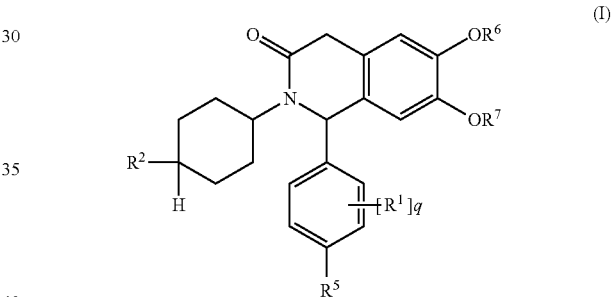

wherein
$R^1$ is halogen or cyano
q is 0, 1 or 2;
$R^2$ is:
  H,
  $R^8(R^9)N—$,
  $R^{10}—C(O)—$, or

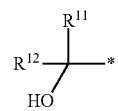

where * marks the point of attachment to the rest of the molecule;
$R^5$ is halo or cyano;
$R^6$ is
  $(C_1-C_4)$alkyl, wherein optionally one, several, or all of the hydrogen atoms are replaced with deuterium, and wherein said $(C_1-C_4)$alkyl is optionally substituted with 1, 2, 3 or 4 halo substituents, or
  $(C_1-C_4)$alkoxy$(C_1-C_4)$alkyl-;
$R^7$ is $(C_1-C_7)$alkyl, wherein optionally one, several, or all of the hydrogen atoms are replaced with deuterium;

$R^8$ is
   H,
   $(C_1-C_4)$alkyl, wherein said $(C_1-C_4)$alkyl is optionally substituted with 1, 2 or 3 substituents independently selected from halo, cyano and OH,
   $(C_1-C_4)$alkyl-C(O)—, wherein said $(C_1-C_4)$alkyl-C(O)— is optionally substituted with 1, 2 or 3 substituents independently selected from halo, cyano and OH,
   $R^{13}(R^{14})N-C(O)-(CH_2)_n-$, or
   HC(O)—
$R^9$ is H, heterocyclyl$^2$, or $(C_1-C_7)$alkyl, said $(C_1-C_7)$alkyl being optionally substituted with 1, 2 or 3 substituents independently selected from halo, cyano and OH;
or $R^8$ and $R^9$ together with the nitrogen atom to which they are attached form heterocyclyl$^1$, said heterocyclyl$^1$ being optionally substituted by 1 or 2 substituents independently selected from $(C_1-C_4)$alkyl and =O;
heterocyclyl$^1$ is a 4, 5 or 6 membered saturated or partially unsaturated monocyclic ring, comprising ring carbon atoms and optionally 1 ring heteroatom independently selected from N, O and S in addition to the ring N atom to which $R^8$ and $R^9$ are attached;
$R^{10}$ is
   H,
   $(C_1-C_6)$alkyl, wherein said $(C_1-C_6)$alkyl is optionally substituted with 1, 2 or 3 substituents independently selected from halo, cyano and OH,
   heterocyclyl$^2$,
   phenyl, said phenyl being optionally substituted with 1 or 2 substituents independently selected from halo, cyano, OH and $(C_1-C_4)$alkyl, said $(C_1-C_4)$alkyl being optionally substituted with 1, 2 or 3 halo substituents, or
   heteroaryl$^2$, said heteroaryl$^2$ being optionally substituted with 1 or 2 substituents independently selected from halo and $(C_1-C_4)$alkyl, wherein said $(C_1-C_4)$alkyl is optionally substituted with 1, 2 or 3 substituents independently selected from halo, cyano and OH;
$R^{11}$ is
   H,
   $(C_1-C_7)$alkyl, wherein said $(C_1-C_7)$alkyl is optionally substituted with 1, 2 or 3 substituents independently selected from halo, cyano and OH,
   heterocyclyl$^2$,
   phenyl, said phenyl being optionally substituted with 1 or 2 substituents independently selected from halo, cyano, OH and $(C_1-C_4)$alkyl, said $(C_1-C_4)$alkyl being optionally substituted with 1, 2 or 3 halo substituents,
   heteroaryl$^1$, said heteroaryl$^1$ being optionally substituted with 1 or 2 substituents independently selected from halo and $(C_1-C_4)$alkyl, wherein said $(C_1-C_4)$alkyl is optionally substituted with 1, 2 or 3 substituents independently selected from halo, cyano and OH,
   $R^{13}(R^{14})N-C(O)-(CH_2)_m-$,
m is 1 or 2;
heterocyclyl$^2$ is a 4, 5 or 6 membered saturated or partially saturated monocyclic group comprising ring carbon atoms and 1 or 2 ring heteroatoms independently selected from N, O and S;
heteroaryl$^1$ is a 5 or 6 membered fully unsaturated monocyclic group comprising ring carbon atoms and 1, 2, 3 or 4 ring heteroatoms independently selected from N, O and S, wherein the total number of ring S atoms does not exceed 1, and the total number of ring O atoms does not exceed 1;
heteroaryl$^2$ is a 5 membered fully unsaturated monocyclic group comprising ring carbon atoms and 1, 2, 3 or 4 ring heteroatoms independently selected from N, O and S, wherein the total number of ring S atoms does not exceed 1, and the total number of ring O atoms does not exceed 1;
$R^{12}$ is H, $(C_1-C_4)$alkyl, wherein said $(C_1-C_4)$alkyl is optionally substituted with 1, 2 or 3 substituents independently selected from halo, cyano and OH;
$R^{13}$ is H or $(C_1-C_4)$alkyl, wherein said $(C_1-C_4)$alkyl is optionally substituted with 1, 2 or 3 substituents independently selected from halo, cyano and OH;
$R^{14}$ is H or $(C_1-C_4)$alkyl, wherein said $(C_1-C_4)$alkyl is optionally substituted with from one to three substituents independently selected from halo, cyano and OH;
n is 0, 1, 2 or 3;
or a salt thereof.

Unless specified otherwise, the term "compounds of the present invention" refers to compounds of formula (I) and subformulae thereof (add other additional genus structures as necessary), prodrugs thereof, salts of the compound and/or prodrugs, hydrates or solvates of the compounds, salts and/or prodrugs, as well as all stereoisomers (including diastereoisomers and enantiomers), tautomers and isotopically labeled compounds (including deuterium substitutions), as well as inherently formed moieties (e.g., polymorphs, solvates and/or hydrates), as well as N-oxides of the compounds of formula (I).

Various embodiments of the invention are described herein. It will be recognized that features specified in each embodiment may be combined with other specified features to provide further embodiments.

In another embodiment, $R^2$ is:

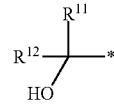

In a further embodiment, $R^2$ is:

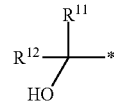

wherein $R^{12}$ is methyl and $R^{11}$ is $(C_1-C_5)$alkyl, and in particular wherein $R^2$ is $CH_3-CH(CH_3)-CH_2-C(OH)(CH_3)-$, $CH_3CH_2CH_2-C(OH)(CH_3)-$, $CH_3CH_2CH_2CH_2-C(OH)(CH_3)-$, or $CH_3-CH(CH_3)-CH_2CH_2-C(OH)(CH_3)-$.

In another embodiment, $R^5$ is chloro.
In another embodiment, q is 0.
In another embodiment, $R^6$ is $(C_1-C_4)$alkyl.
In a further embodiment, $R^6$ is methyl.
In another embodiment, $R^7$ is $(C_1-C_4)$alkyl
In a further embodiment, $R^7$ is isopropyl.
In another embodiment, $R^8$ is
   $(C_1-C_4)$alkyl, wherein said $(C_1-C_4)$alkyl is optionally substituted with OH,
   $(C_1-C_4)$alkyl-C(O)—, wherein said $(C_1-C_4)$alkyl-C(O)— is optionally substituted with OH,
   $R^{13}(R^{14})N-C(O)-$, or
   HC(O)—.

In another embodiment, $R^9$ is H, heterocyclyl$^2$ or $(C_1-C_4)$alkyl, said $(C_1-C_4)$alkyl being optionally substituted by OH.

In another embodiment, $R^8$ and $R^9$ together with the nitrogen atom to which they are attached form heterocyclyl$^1$, said heterocyclyl$^1$ being optionally substituted by 1 =O substituent.

In another embodiment, $R^{10}$ is H, $(C_1-C_4)$alkyl, heterocyclyl$^2$ or phenyl, said phenyl being optionally substituted with 1 or 2 substituents independently selected from halo. In a further embodiment $R^{10}$ is H, methyl, heterocyclyl$^2$ or phenyl substituted by one or two fluoro substituents. In a particular embodiment when $R^{10}$ is phenyl, said phenyl is 3-substituted with fluoro.

In another embodiment, $R^{11}$ is:

H $(C_1-C_6)$alkyl, wherein said $(C_1-C_6)$alkyl is optionally substituted with OH, heterocyclyl$^2$, phenyl substituted by one or two fluoro substituents, and in particular phenyl which is 3-substituted with fluoro, heteroaryl$^1$, or $R^{13}(R^{14})N—C(O)—(CH_2)_2—$.

In another embodiment, $R^{12}$ is H, methyl or ethyl.

In another embodiment, $R^{13}$ is H or methyl.

In another embodiment, $R^{14}$ is H or methyl.

In another embodiment, $R^{12}$ is methyl and $R^{11}$ is $(C_1-C_5)$alkyl.

In another embodiment, heterocyclyl$^1$ is a 5 membered saturated monocyclic ring, comprising ring carbon atoms and optionally 1 ring heteroatom independently selected from N, O and S in addition to the ring N atom to which $R^8$ and $R^9$ are attached. In a further embodiment the additional ring heteroatom is N. In a particular embodiment, heterocyclyl$^1$ is imidazolidinyl, for example imidazolidin-1-yl, in particular 2-oxo-imidazolidin-1-yl.

In another embodiment, heterocyclyl$^2$ is a 6 membered saturated monocyclic group comprising ring carbon atoms and 1 or 2 ring heteroatoms independently selected from N, O and S. In particular heterocyclyl$^2$ contains carbon atoms and 1 O atom. More particularly, heterocyclyl$^2$ is tetrahydropyranyl, even more particularly tetrahydropyran-4-yl.

In another embodiment, heteroaryl$^1$ is a 5 membered fully unsaturated monocyclic group comprising ring carbon atoms and 1 ring N heteroatom or 1 ring O heteroatom. In a further embodiment, is pyrrol-3-yl or furan-3-yl.

In another embodiment n is 0.

In another embodiment m is 2.

In another embodiment, the stereochemistry of the compound of formula (I) is as shown in formula (Ia) below:

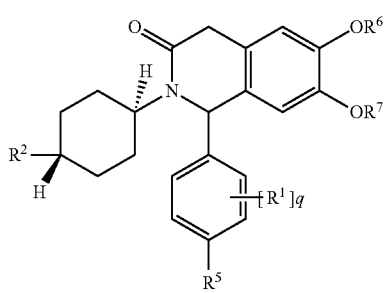

(Ia)

In another embodiment, the stereochemistry of the compound of formula (I) when $R^2$ is

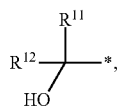

is as shown below:

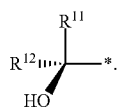

For example, in one embodiment $R^2$ is

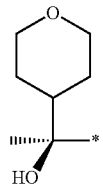

In a further embodiment, $R^2$ is preferably H, $CH_3—C(O)—N(CH_3)—$, $CH_3—C(O)—N(CH_2CH_3)—$, $CH_3—C(O)—NH—$, $HO—CH_2CH_2—N(CH_3)—$, $H_2N—C(O)—NH—$, $H_2N—C(O)—N(CH_3)—$, $HO—CH_2CH_2—C(O)—N(CH_3)—$, $CH_3—C(O)—N(CH_2CH_2CH_3)$, $HC(O)—N(CH_2CH_2CH_3)$, $CH_3—C(O)—N(CH_2CH_2CH_2CH_3)$, $CH_3—C(O)—N(CH_2CH_2CH(OH))$, $CH_3—C(O)—$, $CH_3—C(CH_3)(OH)—$, tetrahydropyran-4-yl-CH(OH)—, tetrahydropyran-4-yl-C(O)—, tetrahydropyran-4-yl-C(CH_3)(OH)—, 3-fluorophenyl-CH(OH)—, 3-fluorophenyl-C(O)—, 3-fluorophenyl-C(CH_3)(OH)—, 3-fluorophenyl-C(CH_2CH_3)(OH)—, $CH_3—CH(CH_3)—CH_2—C(OH)(CH_3)—$, $CH_3CH_2CH_2—C(OH)(CH_3)—$, $CH_3CH_2CH_2CH_2—C(OH)(CH_3)—$, $CH_3—CH(CH_3)—CH_2CH_2—C(OH)(CH_3)—$, furan-3-yl-C(CH_3)(OH)—, $CH_3CH_2CH(CH_3)CH_2—C(OH)(CH_3)—$, $H_2N—C(O)—CH_2CH_2—C(OH)(CH_3)—$, $H(CH_3)N—C(O)—CH_2CH_2—C(OH)(CH_3)—$, 1-methylpyrrol-3-yl-C(OH)(CH_3)—, 2-hydroxyethyl-1H-pyrrol-3-yl-C(OH)(CH_3)—, or

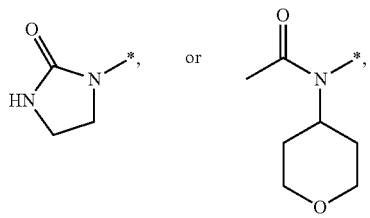

In another embodiment there is provided a compound, or compounds, of formula (I) selected from the following list:
1: 1-(4-Chloro-phenyl)-2-cyclohexyl-7-isopropoxy-6-methoxy-1,4-dihydro-2H-isoquinolin-3-one
2: N-{4-[1-(4-Chloro-phenyl)-7-isopropoxy-6-methoxy-3-oxo-3,4-dihydro-1H-isoquinolin-2-yl]-cyclohexyl}-N-methyl-acetamide 3: N-{4-[1-(4-Chloro-phenyl)-7-isopropoxy-6-methoxy-3-oxo-3,4-dihydro-1H-isoquinolin-2-yl]-cyclohexyl}-N-ethyl-acetamide
4: N-{4-[1-(4-Chloro-phenyl)-7-isopropoxy-6-methoxy-3-oxo-3,4-dihydro-1H-isoquinolin-2-yl]-cyclohexyl}-acetamide
5: 1-(4-Chloro-phenyl)-2-{4-[(2-hydroxy-ethyl)-methyl-amino]cyclohexyl}-7-isopropoxy-6-methoxy-1,4-dihydro-2H-isoquinolin-3-one
6: {4-[1-(4-Chloro-phenyl)-7-isopropoxy-6-methoxy-3-oxo-3,4-dihydro-1H-isoquinolin-2-yl]-cyclohexyl}-urea
7: 1-{4-[1-(4-Chloro-phenyl)-7-isopropoxy-6-methoxy-3-oxo-3,4-dihydro-1H-isoquinolin-2-yl]-cyclohexyl}-1-methyl-urea
8: 1-(4-Chloro-phenyl)-7-isopropoxy-6-methoxy-2-[4-(2-oxo-imidazolidin-1-yl)-cyclohexyl]-1,4-dihydro-2H-isoquinolin-3-one
9: N-{4-[1-(4-Chloro-phenyl)-7-isopropoxy-6-methoxy-3-oxo-3,4-dihydro-1H-isoquinolin-2-yl]-cyclohexyl}-3-hydroxy-N-methyl-propionamide
10: N-{4-[1-(4-Chloro-phenyl)-7-isopropoxy-6-methoxy-3-oxo-3,4-dihydro-1H-isoquinolin-2-yl]-cyclohexyl}-N-propyl-acetamide
11: N-{4-[1-(4-Chloro-phenyl)-7-isopropoxy-6-methoxy-3-oxo-3,4-dihydro-1H-isoquinolin-2-yl]-cyclohexyl}-N-propyl-formamide
12: N-Butyl-N-{4-[1-(4-chloro-phenyl)-7-isopropoxy-6-methoxy-3-oxo-3,4-dihydro-1H-isoquinolin-2-yl]-cyclohexyl}-acetamide
13: N-{4-[1-(4-Chloro-phenyl)-7-isopropoxy-6-methoxy-3-oxo-3,4-dihydro-1H-isoquinolin-2-yl]-cyclohexyl}-N-(tetrahydro-pyran-4-yl)-acetamide
14: N-{4-[1-(4-Chloro-phenyl)-7-isopropoxy-6-methoxy-3-oxo-3,4-dihydro-1H-isoquinolin-2-yl]-cyclohexyl}-N-(3-hydroxy-propyl)-acetamide
15: 2-(4-Acetyl-cyclohexyl)-1-(4-chloro-phenyl)-7-isopropoxy-6-methoxy-1,4-dihydro-2 H-isoquinolin-3-one
16: 1-(4-Chloro-phenyl)-2-[4-(1-hydroxy-1-methyl-ethyl)-cyclohexyl]-7-isopropoxy-6-methoxy-1,4-dihydro-2H-isoquinolin-3-one
17: 1-(4-Chloro-phenyl)-2-{4-[hydroxy-(tetrahydro-pyran-4-yl)-methyl]-cyclohexyl}-7-isopropoxy-6-methoxy-1,4-dihydro-2H-isoquinolin-3-one
18: 1-(4-Chloro-phenyl)-7-isopropoxy-6-methoxy-2-[4-(tetrahydro-pyran-4-carbonyl)-cyclohexyl]-1,4-dihydro-2H-isoquinolin-3-one
19: (S)-1-(4-Chloro-phenyl)-7-isopropoxy-6-methoxy-2-[4-(tetrahydro-pyran-4-carbonyl)-cyclohexyl]-1,4-dihydro-2H-isoquinolin-3-one
20: (R)-1-(4-Chloro-phenyl)-7-isopropoxy-6-methoxy-2-[4-(tetrahydro-pyran-4-carbonyl)-cyclohexyl]-1,4-dihydro-2H-isoquinolin-3-one
21: 1-(4-Chloro-phenyl)-2-{4-[1-hydroxy-1-(tetrahydro-pyran-4-yl)-ethyl]-cyclohexyl}-7-isopropoxy-6-methoxy-1,4-dihydro-2H-isoquinolin-3-one
22: (S)-1-(4-Chloro-phenyl)-2-{4-[(R)-1-hydroxy-1-(tetrahydro-pyran-4-yl)-ethyl]-cyclohexyl}-7-isopropoxy-6-methoxy-1,4-dihydro-2H-isoquinolin-3-one
23: (S)-1-(4-Chloro-phenyl)-2-{4-[(S)-1-hydroxy-1-(tetrahydro-pyran-4-yl)-ethyl]-cyclohexyl}-7-isopropoxy-6-methoxy-1,4-dihydro-2H-isoquinolin-3-one
24: 1-(4-Chloro-phenyl)-2-{4-[(3-fluoro-phenyl)-hydroxy-methyl]-cyclohexyl}-7-isopropoxy-6-methoxy-1,4-dihydro-2H-isoquinolin-3-one
25: 1-(4-Chloro-phenyl)-2-[4-(3-fluoro-benzoyl)-cyclohexyl]-7-isopropoxy-6-methoxy-1,4-dihydro-2H-isoquinolin-3-one
26: 1-(4-Chloro-phenyl)-2-{4-[1-(3-fluoro-phenyl)-1-hydroxy-ethyl]cyclohexyl}-7-isopropoxy-6-methoxy-1,4-dihydro-2H-isoquinolin-3-one
27: 1-(4-Chloro-phenyl)-2-{4-[1-(3-fluoro-phenyl)-1-hydroxy-propyl]-cyclohexyl}-7-isopropoxy-6-methoxy-1,4-dihydro-2H-isoquinolin-3-one
28: 1-(4-Chloro-phenyl)-2-[4-(1-hydroxy-1,3-dimethyl-butyl)-cyclohexyl]-7-isopropoxy-6-methoxy-1,4-dihydro-2H-isoquinolin-3-one
29: 1-(4-Chloro-phenyl)-2-[4-(1-hydroxy-1-methyl-butyl)-cyclohexyl]-7-isopropoxy-6-methoxy-1,4-dihydro-2H-isoquinolin-3-one
30: 1-(4-Chloro-phenyl)-2-[4-(1-hydroxy-1-methyl-pentyl)-cyclohexyl]-7-isopropoxy-6-methoxy-1,4-dihydro-2H-isoquinolin-3-one
31: 1-(4-Chloro-phenyl)-2-[4-(1-hydroxy-1,4-dimethyl-pentyl)-cyclohexyl]-7-isopropoxy-6-methoxy-1,4-dihydro-2H-isoquinolin-3-one, and
32: 1-(4-Chloro-phenyl)-2-[4-(1-furan-3-yl-1-hydroxy-ethyl)-cyclohexyl]-7-isopropoxy-6-methoxy-1,4-dihydro-2H-isoquinolin-3-one or a salt thereof.

For purposes of interpreting this specification, terms used in the singular will also include the plural and vice versa.

In the above definitions, halo means fluoro, chloro or bromo. Particularly fluoro or chloro, especially fluoro.

Alkyl, and alkoxy groups, containing the requisite number of carbon atoms, can be unbranched or branched. Examples of alkyl include, but are not limited to, methyl, ethyl, n-propyl, i-propyl, n-butyl, i-butyl, sec-butyl and t-butyl. Examples of alkoxy include methoxy, ethoxy, n-propoxy, i-propoxy, n-butoxy, i-butoxy, sec-butoxy and t-butoxy.

=O means an oxo substituent. For example, a heterocyclyl ring substituted by an =O substituent means there is an oxo substituent directly on ring.

Specific preferred compounds according to the invention are those listed in the Examples section below As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

p53 refers to the human protein itself as described by Matlashewski et al. in EMBO J. 3, 3257-62 (1984) or related family members (e.g. p73 as described in Kaghad et al. in Cell 90, 809-19 (1997) and p63 as described in Yang et al in Mol Cell 2, 305-16 (1998)) (named also p53 wild type herein) or to any variant thereof (e.g. a splice variant, mutant, fragment or isoform due to deletion, insertion and/or exchange of one or more, e.g. one to 200, of the amino acids) that is still capable to retain preferably at least 1%, more preferably at least 5%, yet more preferably at least 10%, 20%, 30%, 40%, 50% or more than 50% of the p53 activity in growth suppression, e.g. in the growth suppression assay described in Pietenpol et al., Proc. Nat. Acad. Sci. USA 91, 1998-2002 (1994) and, if compared with the corresponding sequence of p53 wild type, shows at least 20%, more preferably at least 25% identity with the full sequence, e.g. at least 90% identity with a partial sequence thereof. Where not mentioned otherwise, p53 generally relates to TP53, p53, TP73, p73, TP63, TP73L, p63, or variants thereof, respectively, as just defined.

As already indicated above, MDM2 (especially when mentioned as MDM2 or variants thereof) generally refers to all genes and/or proteins encoded thereof with the names MDM2, Mdm2, HDM2, Hdm2, or a variant thereof. MDM4 (especially when mentioned as MDM4 or variants thereof) refers to all genes and/or proteins encoded thereof with the names MDM4, Mdm4, HDM4, Hdm4, MDMX, MdmX, HDMX, HdmX, or a variant thereof.

MDM2 specifically relates to MDM2 as described in EMBO J. 10, 1565-9, Fakharzadeh et al., 1991, a variant thereof refers to a variant thereof which still binds to p53 in the assay system described below (e.g. a splice variant, isoform, fragment, mutant or oncogene due to deletion, insertion and/or exchange of one or more, e.g. one to 430, of the amino acids), corresponding to the full length proteins as originally described, preferably at least with 0.5%, more preferably at least with 5%, 10%, 20%, 30%, 40% or especially 50% or more of the affinity of MDM2 to p53, and have at least 20%, more preferably at least 25%, sequence identity to MDM2 or to HDM2 as originally described or as mentioned below specifically. Where not mentioned otherwise, MDM2 generally relates to MDM2, Mdm2, HDM2 or Hdm2, or variants thereof, respectively, as just defined.

MDM4 specifically relates to MDM4 as described in Genomics 43, 34-42, Shvarts et al., 1997, a variant thereof refers to a variant thereof which still binds to p53 in the assay system described below (e.g. a splice variant, isoform, fragment, mutant or oncogene due to deletion, insertion and/or exchange of one or more, e.g. one to 430, of the amino acids), corresponding to the full length proteins as originally described, preferably at least with 0.5%, more preferably at least with 5%, 10%, 20%, 30%, 40% or especially 50% or more of the affinity of MDM4 to p53, and have at least 20%, more preferably at least 25%, sequence identity to MDM4, to MDMX, to HDM4 or to HDM2 as originally described or as mentioned below specifically. Where not mentioned otherwise, MDM4 generally relates to MDM4, Mdm4, HDM4, Hdm4, MDMX, MdmX, HDMX or HdmX, or variants thereof, respectively, as just defined.

The percentage of sequence identity, often also termed homology, between a protein and a variant thereof is preferably determined by a computer program commonly employed for this purpose, such as the Gap program (Wisconsin Sequence Analysis Package, Version 8 for Unix, Genetics Computer Group, University Reseach Park, Madison Wis., USA, which uses the algorithm of Smith and Waterman (Adv. Appl. Math. 2: 482-489 (1981), especially using an affine gap search with a gap open penalty of 12 and a gap extension penalty of 1.

"Variants thereof" where mentioned means one or more variant(s).

A proto-oncogene is a normal gene that can become an oncogene, either after mutation or increased expression. Proto-oncogenes code for proteins that help to regulate cell growth and differentiation. Proto-oncogenes are often involved in signal transduction and execution of mitogenic signals, usually through their protein products. Upon activation, a proto-oncogene (or its product) becomes a tumor inducing agent, an oncogene.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by MDM2 and/or MDM4, or (ii) associated with MDM2 and/or MDM4 activity, or (iii) characterized by activity (normal or abnormal) of MDM2 and/or MDM4, or (2) reducing or inhibiting the activity of MDM2 and/or MDM4, or (3) reducing or inhibiting the expression of MDM2 and/or MDM4. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of MDM2 and/or MDM4; or at least partially reducing or inhibiting the expression of MDM2 and/or MDM4.

In a further embodiment, the compounds of formula (I) are particularly useful for the treatment of disorders of diseases associated with the activity of MDM2.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

In another embodiment of the invention there is provided a pharmaceutical composition comprising a therapeutically effective amount of a compound of formula (I) as defined herein, and one or more pharmaceutically acceptable carriers.

In another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc. Typically, the pharmaceutical compositions are tablets or gelatin capsules comprising the active ingredient together with a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be desirable.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by the following in vitro & in vivo methods.

The compounds of formula I in free form or in salt form exhibit valuable pharmacological properties, e.g. MDM2 and/or MDM4 modulating properties, e.g. as indicated in tests as provided in the next sections, and are therefore indicated for therapy.

Having regard to their inhibitory effect on p53/MDM2 and/or p53/MDM4 interaction, compounds of the formula (I) in free or pharmaceutically acceptable salt form, are useful in the treatment of conditions which are mediated by the activity (including normal activity or especially overactivity) of MDM2 and/or MDM4, or variants thereof, respectively, as described, such as proliferative conditions, e.g. by activation of the P53/MDM2 interaction, and/or that are responsive (meaning especially in a therapeutically beneficial way) to inhibition of the p53/MDM2 interaction, most especially a disease or disorder as mentioned hereinbelow.

Compounds of formula (I) are believed to be useful in the treatment of a disease based on dysregulation of cell cycle, such as a proliferative disorder or disease, for example cancer or tumour diseases. In particular, such diseases or disorders include benign or malignant tumors, a sarcoma, such as liposarcoma, rhabdomyosarcoma or bone cancer, e.g. osteosarcomas, a carcinoma, such as of the brain, kidney, liver, adrenal gland, bladder, breast, gastric, ovary, colon, rectum, prostate, pancreas, lung, vagina or thyroid, a glioblastoma, a multiple myeloma, a gastrointestinal cancer, especially colon carcinoma or colorectal adenoma, a tumor of the head and neck, a melanoma, a prostate hyperplasia, a neoplasia, a neoplasia of epithelial character, a leukemia or a lymphoma, such as of B- or T-cell origin, and metastases in other organs), viral infections (e.g. herpes, papilloma, HIV, Kaposi's, viral hepatitis).

In particular, compounds of formula (I) are believed to be useful to treat a sarcoma such as liposarcoma, rhabdomyosarcoma or osteosarcoma, or a melanoma, leukemia or lymphoma.

Thus, as a further embodiment, the present invention provides the use of a compound of formula (I) in therapy. In a further embodiment, the therapy is selected from a disease which may be treated by inhibition of the MDM2/p53 and/or MDM4/p53 interaction, in particular the diseases or disorders listed herein.

The invention also provides a compound of the formula (I) as defined herein, for use as a pharmaceutical, in particular for use in the treatment of a disorder or a disease mediated by the activity of MDM2 and/or MDM4, in particular for a disease or disorder mentioned herein.

The invention also provides the use of a compound of formula (I) as defined herein, for the manufacture of a medicament for the treatment of a disorder or a disease in a subject mediated by the activity of MDM2 and/or MDM4, more particularly for a disease or disorder mentioned herein.

In another embodiment, the invention provides a method of treating a disease or disorder which is treated by inhibition of the MDM2/p53 and/or MDM4/p53 interaction, comprising administration of a therapeutically acceptable amount of a compound of formula (I), in particular a method of treating the diseases or disorders listed herein.

In another embodiment, the invention provides a method of modulating MDM2 and/or MDM4 activity in a subject, comprising the step of administering to a subject a therapeutically effective amount of a compound of formula (I) as defined herein.

The compounds of the formula (I) have advantageous pharmacological properties and disturb the binding interaction (also referred to herein as p53/MDM2 and p53/MDM4 interaction or as p53/MDM2 interaction solely) between p53 on the one side and MDM2 and/or MDM4 or (especially oncogenic) variants thereof which still are capable of binding to p53, on the other side.

The invention also relates to the use of a compound of the formula (I) (or a pharmaceutical formulation comprising a compound of the formula (I)) in the treatment of one or more of the diseases mentioned above and below where the disease (s) respond or responds (in a beneficial way, e.g. by partial or complete removal of one or more of its symptoms up to complete cure or remission) to an inhibition of the MDM2/p53 and/or MDM4/p53 interaction, especially where the involved MDM2 or MDM4 and/or variant shows (e.g. in the context of other regulatory mechanisms, due to overexpression, to mutation or the like) inadequately high or more higher than normal activity.

The invention can also relate to the use of a compound of the formula (I) to induce cell cycle deceleration or preferably arrest and/or apoptosis in cells containing p53 or variants thereof that are still functional, for sensitizing cells to one or more additional pharmaceutically active agents, such as inducers of apoptosis and/or of cell cycle deceleration or arrest, and to chemoprotection of normal cells through the induction of cell cycle deceleration or arrest prior to treatment with one or more other chemotherapeutic agents, to the use in rendering normal cells resistant to chemotherapeutic agents and/or treatments, and/or the use in protecting cells from toxic side effects of chemotherapeutic agents or treatments, such as side effects resulting in mucositis, stomatitis, xerostomia, gastrointestinal disorders and/or alopecia.

The efficacy of the compounds of the formula (I) and salts thereof as modulators affecting the interaction between can be demonstrated as shown in WO 98/01467 (which especially regarding the assays is included herein by reference) or preferably follows:

Assays

Time Resolved Fluorescence Energy Transfer (TR-FRET) Assay

The inhibition of p53-MDM2 and p53-MDM4 interactions is measured by time resolved fluorescence energy transfer (TR-FRET). Fluorescence energy transfer (or Foerster resonance energy transfer) describes an energy transfer between donor and acceptor fluorescent molecules. For this assay, human MDM2 protein (amino acids 2-188) and human MDM4 protein (amino acids 2-185), tagged with a C-terminal biotin moiety, are used in combination with a Europium labeled streptavidin (Perkin Elmer, Inc., Waltham, Mass., USA) serving as the donor fluorophore. The p53 derived, Cy5 labeled peptide Cy5-TFSDLWKLL (p53 aa18-26) is the energy acceptor. Upon excitation of the donor molecule at 340 nm, binding interaction between MDM2 or MDM4 and the p53 peptide induces energy transfer and enhanced response at the acceptor emission wavelength at 665 nm.

Disruption of the formation of the p53-MDM2 or p53-MDM4 complex due to an inhibitor molecule binding to the p53 binding site of MDM2 or MDM4 results in increased donor emission at 620 nm. The ratiometric FRET assay readout is calculated from the raw data of the two distinct fluorescence signals measured in time resolved mode (fluorescence 665 nm/fluorescence 620 nm×1000).

The test is performed in white 384-well plates (Greiner Bio-One, reference 781207) in a total volume of 60 μL by adding 1 μL of compounds tested at different concentrations diluted in 100% DMSO (1.7% final DMSO concentration) in reaction buffer (PBS, 125 mM NaCl, 0.001% Novexin (consists of carbohydrate polymers), designed to increase the solubility and stability of proteins; Expedeon Ltd., Cambridgeshire, United Kingdom), 0.01% Gelatin, 0.01% 0.2%, Pluronic F-127 (block copolymer from ethylenoxide and propyleneoxide), 1 mM DTT). After addition of 1.25 nM MDM2-biotinylated or 2.5 nM MDM4-biotinylated (internal preparations), and 0.625 nM Europium labeled streptavidin (PerkinElmer), the solution is pre-incubated for 15 minutes at room temperature, then 10 nM Cy5-p53 peptide (internal preparation) is added before an incubation at room temperature for 15 minutes prior to reading the plate. For measurement of samples, a Victor II microplate reader (Perkin Elmer) is used with the following settings: Excitation 340 nm, Emission Donor 620 nm and Emission Acceptor 665 nm. $IC_{50}$ values are calculated by curve fitting using XLfit. If not specified, reagents are purchased from Sigma-Aldrich Chemie GmBH, Buchs, Switzerland.

This assay was used to evaluate compounds displaying inhibition of p53-MDM2 interaction and p53-MDM4 interaction at $IC_{50}$s of 0.005 to 50 μM (p53-MDM2 Assay 1 and p53-MDM4 Assay 1, respectively). For selected compounds displaying $IC_{50}$s between 0.05 and 5 nM on MDM2, a slightly modified assay is used with the following adaptations: 0.1 nM MDM2, 0.1 nM Europium labeled streptavidin and Tecan genios Pro is used as a microplate reader for the fluorescence measurements (p53-MDM2 Assay 2).

The present invention also relates to novel aspects of the above described assays. Inhibitions of p53-Hdm2 and p53-Hdm4 by representative compounds in the present invention are displayed herein.

Cellular Proliferation Assay in SJSA-1 and SAOS-2 Cells Based on YO-PRO®-1 Iodide Staining The effect of PPI (protein-protein interaction) inhibitors on cell growth of p53 wild-type or mutant cells is assessed in a proliferation assay based on YO-PRO®-1 iodide staining (J Immunol Methods. 1995; 185(2):249-58). The principal of this assay is the use of the DNA-intercalating dye YO-PRO®-1 iodide which upon binding to DNA emits a strong fluorescence signal. In addition, the dye is membrane-impermeant and thus, apoptotic cells can be distinguished from the viable cell population during the same assay. In the absence of cell permeabilization, the dye is only entering into cells that are beginning to undergo apoptosis. After treatment of the cells with a lysis buffer, the total cell number can be estimated.

To test PPI inhibitors on cell growth, SJSA-1 cells (p53 wild-type cells) and SAOS-2 cells (p53 null cells) are plated out into 96-well micro-titer plates and treated with decreasing concentrations of the compounds. After a 72 hour incubation period, 2.5 μM YO-PRO®-1 iodide is directly added to the cells and a first read-out is performed using a standard fluorescence plate reader (filter setting 485/530 nm) revealing the relative number of apoptotic cells. Subsequently, cells are permeabilized by directly adding lysis buffer containing the detergent NP40, EDTA and EGTA to obtain final concentrations of 0.01% and 5 mM, respectively. After complete permeabilization, the total cell number is quantified during a second read using the fluorescence plate reader with the same settings.

In Vivo Experiments

There are also experiments that can demonstrate the anti-tumor activity of compounds of the formula (I) in vivo.

For example, female Harlan (Indianapolis, Ind., USA) athymic nu/nu mice with s.c. transplanted human osteosarcoma SJSA-1 tumors can be used to determine the anti-tumor activity of p53/MDM2 interaction inhibitors. On day 0, with the animals under peroral Forene® (1-chloro-2,2,2-trifluoro-ethyldifluormethylether, Abbot, Wiesbaden, Germany) narcosis, $3 \times 10^6$ cells are injected under the skin on the animals' left flank. When tumors reach a volume of 100 mm$^3$, the mice are divided at random into groups of 6-8 animals and treatment commences. The treatment is carried out for a 2-3 weeks period with peroral, intravenous or intra-peritoneal administration twice daily (or less frequently) of a compound of the formula (I) in a suitable vehicle at defined doses. The tumors are measured twice a week with a slide gauge and the volume of the tumors is calculated.

As an alternative to cell line SJSA-1, other cell lines may also be used in the same manner, for example, the HCT116 colon carcinoma cell line (ATCC No. CCL-247);

the LNCaP clone FGC prostate carcinoma cell line (ATCC No. CRL-1740);

the RKO colon carcinoma cell line (ATCC No. CRL-2577);

the HT1080 fibrosarcoma cell line (ATCC No. CCL-121);

the A375 malignant melanoma cell line (ATCC No. CRL-1619), the NCI-H460 large cell lung carcinoma cell line (ATCC No. HTB-177);

the JEG-3 choriocarcinoma (ATCC No. HTB-36)

the ZR-75-1 breast ductal carcinoma (ATCC No. CRL-1500)

A compound of the formula (I) may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibittors; mTOR inhibitors, such as RAD001; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies, such as HCD122; heparanase inhibitors; inhibitors of Ras oncogenic isoforms; telomerase inhibitors; proteasome inhibitors; compounds used in the treatment of hematologic malignancies, such as fludarabine; compounds which target, decrease or inhibit the activity of Flt-3, such as PKC412; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics and AUY922; temozolomide (TEMODAL™); kinesin spindle protein inhibitors, such as SB715992 or SB743921 from GlaxoSmithKline, or pentamidine/chlorpromazine from CombinatoRx; PI3K inhibitors, such as BEZ235; RAF inhibitors, such as RAF265; MEK inhibitors such as ARRY142886 from Array PioPharma, AZD6244 from AstraZeneca, PD181461 from Pfizer, leucovorin, antileukemia compounds, ribonucleotide reductase inhibittors, S-adenosylmethionine decarboxylase inhibitors, regulators of apoptosis, antiproliferative antibodies or other chemotherapeutic compounds. Further, alternatively or in addition they may be used in combination with other tumor treatment approaches, including surgery, ionizing radiation, photodynamic therapy, implants, e.g. with corticosteroids, hormones, or they may be used as radiosensitizers. Also, in anti-inflammatory and/or antiproliferative treatment, combination with anti-inflammatory drugs is included. Combination is also possible with antihistamine drug substances, bronchodilatatory drugs, NSAID or antagonists of chemokine receptors.

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketoconazole, vorozole, fadrozole, anastrozole and letrozole. Exemestane can be administered, e.g., in the form as it is marketed, e.g. under the trademark AROMASIN. Formestane can be administered, e.g., in the form as it is marketed, e.g. under the trademark LENTARON. Fadrozole can be administered, e.g., in the form as it is marketed, e.g. under the trademark AFEMA. Anastrozole can be administered, e.g., in the form as it is marketed, e.g. under the trademark ARIMIDEX. Letrozole can be administered, e.g., in the form as it is marketed, e.g. under the trademark FEMARA or FEMAR. Aminoglutethimide can be administered, e.g., in the form as it is marketed, e.g. under the trademark ORIMETEN. A combination of the invention comprising a chemotherapeutic agent which is an aromatase inhibitor is particularly useful for the treatment of hormone receptor positive tumors, e.g. breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX. Raloxifene hydrochloride can be administered, e.g., in the form as it is marketed, e.g. under the trademark EVISTA. Fulvestrant can be formulated as disclosed in U.S. Pat. No. 4,659,516 or it can be administered, e.g., in the form as it is marketed, e.g. under the trademark FASLODEX. A combination of the invention comprising a chemotherapeutic agent which is an antiestrogen is particularly useful for the treatment of estrogen receptor positive tumors, e.g. breast tumors.

The term "anti-androgen" as used herein relates to any substance which is capable of inhibiting the biological effects of androgenic hormones and includes, but is not limited to, bicalutamide (CASODEX™), which can be formulated, e.g. as disclosed in U.S. Pat. No. 4,636,505.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX. Abarelix can be formulated, e.g. as disclosed in U.S. Pat. No. 5,843,901.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148 (compound A1 in WO99/17804). Irinotecan can be administered, e.g. in the form as it is marketed, e.g. under the trademark CAMPTOSAR. Topotecan can be administered, e.g., in the form as it is marketed, e.g. under the trademark HYCAMTIN.

The term "topoisomerase II inhibitor" as used herein includes, but is not limited to the anthracyclines such as doxorubicin (including liposomal formulation, e.g. CAELYX), daunorubicin, epirubicin, idarubicin and nemorubicin, the anthraquinones mitoxantrone and losoxantrone, and the podophillotoxines etoposide and teniposide. Etoposide can be administered, e.g. in the form as it is marketed, e.g. under the trademark ETOPOPHOS. Teniposide can be administered, e.g. in the form as it is marketed, e.g. under the trademark VM 26-BRISTOL. Doxorubicin can be administered, e.g. in the form as it is marketed, e.g. under the trademark ADRIBLASTIN or ADRIAMYCIN. Epirubicin can be administered, e.g. in the form as it is marketed, e.g. under the trademark FARMORUBICIN. Idarubicin can be administered, e.g. in the form as it is marketed, e.g. under the trademark ZAVEDOS. Mitoxantrone can be administered, e.g. in the form as it is marketed, e.g. under the trademark NOVANTRON.

The term "microtubule active compound" relates to microtubule stabilizing, microtubule destabilizing compounds and microtublin polymerization inhibitors including, but not limited to taxanes, e.g. paclitaxel and docetaxel, vinca alkaloids, e.g., vinblastine, especially vinblastine sulfate, vincristine especially vincristine sulfate, and vinorelbine, discodermolides, cochicine and epothilones and derivatives thereof, e.g. epothilone B or D or derivatives thereof. Paclitaxel may be administered e.g. in the form as it is marketed, e.g. TAXOL™. Docetaxel can be administered, e.g., in the form as it is marketed, e.g. under the trademark TAXOTERE. Vinblastine sulfate can be administered, e.g., in the form as it is marketed, e.g. under the trademark VINBLASTIN R. P. Vincristine sulfate can be administered, e.g., in the form as it is marketed, e.g. under the trademark FARMISTIN. Discodermolide can be obtained, e.g., as disclosed in U.S. Pat. No. 5,010,099. Also included are Epothilone derivatives which are disclosed in WO 98/10121, U.S. Pat. No. 6,194,181, WO 98/25929, WO 98/08849, WO 99/43653, WO 98/22461 and WO 00/31247. Especially preferred are Epothilone A and/or B.

The term "alkylating compound" as used herein includes, but is not limited to, cyclophosphamide, ifosfamide, melphalan or nitrosourea (BCNU or Gliadel). Cyclophosphamide can be administered, e.g., in the form as it is marketed, e.g. under the trademark CYCLOSTIN. Ifosfamide can be administered, e.g., in the form as it is marketed, e.g. under the trademark HOLOXAN.

The term "antineoplastic antimetabolite" includes, but is not limited to, 5-Fluorouracil or 5-FU, capecitabine, gemcitabine, DNA demethylating compounds, such as 5-azacytidine and decitabine, methotrexate and edatrexate, and folic acid antagonists such as pemetrexed. Capecitabine can be administered, e.g., in the form as it is marketed, e.g. under the trademark XELODA. Gemcitabine can be administered, e.g., in the form as it is marketed, e.g. under the trademark GEMZAR.

The term "platin compound" as used herein includes, but is not limited to, carboplatin, cis-platin, cisplatinum and oxaliplatin. Carboplatin can be administered, e.g., in the form as it is marketed, e.g. under the trademark CARBOPLAT. Oxaliplatin can be administered, e.g., in the form as it is marketed, e.g. under the trademark ELOXATIN.

The term "compounds targeting/decreasing a protein or lipid kinase activity"; or a "protein or lipid phosphatase activity"; or "further anti-angiogenic compounds" as used herein includes, but is not limited to, protein tyrosine kinase and/or serine and/or threonine kinase inhibitors or lipid kinase inhibitors, e.g., a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g. a N-phenyl-2-pyrimidine-amine derivative, e.g. imatinib, SU101, SU6668 and GFB-111;

b) compounds targeting, decreasing or inhibiting the activity of the fibroblast growth factor-receptors (FGFR);

c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, such as those compounds disclosed in WO 02/092599, or antibodies that target the extracellular domain of IGF-I receptor or its growth factors;

d) compounds targeting, decreasing or inhibiting the activity of the Trk receptor tyrosine kinase family, or ephrin B4 inhibitors;

e) compounds targeting, decreasing or inhibiting the activity of the Axl receptor tyrosine kinase family;

f) compounds targeting, decreasing or inhibiting the activity of the Ret receptor tyrosine kinase;

g) compounds targeting, decreasing or inhibiting the activity of the Kit/SCFR receptor tyrosine kinase, i.e C-kit receptor tyrosine kinases—(part of the PDGFR family), such as compounds which target, decrease or inhibit the activity of the c-Kit receptor tyrosine kinase family, especially compounds which inhibit the c-Kit receptor, e.g. imatinib;

h) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, e.g. a N-phenyl-2-pyrimidine-amine derivative, e.g. imatinib or nilotinib (AMN107); PD180970; AG957; NSC 680410; PD173955 from ParkeDavis; or dasatinib (BMS-354825)

i) compounds targeting, decreasing or inhibiting the activity of members of the protein kinase C(PKC) and Raf family of serine/threonine kinases, members of the MEK, SRC, JAK, FAK, PDK1, PKB/Akt, and Ras/MAPK family members, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; LY333531/LY379196; isochinoline compounds such as those disclosed in WO 00/09495; FTIs; BEZ235 (a P13K inhibitor) or AT7519 (CDK inhibitor);

j) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC™) or tyrphostin. A tyrphostin is preferably a low molecular weight (Mr <1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin);

k) compounds targeting, decreasing or inhibiting the activity of the epidermal growth factor family of receptor tyrosine kinases (EGFR, ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180); e.g. trastuzumab (Herceptin™) cetuximab (Erbitux™), Iressa, Tarceva, OSI-774, CI-1033, EKB-569, GW-2016, E1.1, E2.4, E2.5, E6.2, E6.4, E2.11, E6.3 or E7.6.3, and 7H-pyrrolo-[2,3-d]pyrimidine derivatives which are disclosed in WO 03/013541; and l) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF;

m) compounds targeting, decreasing or inhibiting the activity of PI3K, such as BEZ235, BKM120 or BYL719;

n) compounds targeting, decreasing or inhibiting the activity of the cyclin dependent kinase family, such as PD 0332991, or compounds inhibiting the Ras/Raf/MEK pathway such as RAF265, or a MEK inhibitor.

Further anti-angiogenic compounds include compounds having another mechanism for their activity, e.g. unrelated to protein or lipid kinase inhibition e.g. thalidomide (THALOMID) and TNP-470.

Compounds which target, decrease or inhibit the activity of a protein or lipid phosphatase are e.g. inhibitors of phosphatase 1, phosphatase 2A, or CDC25, e.g. okadaic acid or a derivative thereof.

Compounds which induce cell differentiation processes are e.g. retinoic acid, α- γ- or δ-tocopherol or α- γ- or δ-tocotrienol.

The term cyclooxygenase inhibitor as used herein includes, but is not limited to, e.g. Cox-2 inhibitors, 5-alkyl substituted 2-arylaminophenylacetic acid and derivatives, such as celecoxib (CELEBREX™), rofecoxib (VIOXX™), etoricoxib, valdecoxib or a 5-alkyl-2-arylaminophenylacetic acid, e.g. 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. "Etridonic acid" can be administered, e.g., in the form as it is marketed, e.g. under the trademark DIDRONEL. "Clodronic acid" can be administered, e.g., in the form as it is marketed, e.g. under the trademark BONEFOS. "Tiludronic acid" can be administered, e.g., in the form as it is marketed, e.g. under the trademark SKELID. "Pamidronic acid" can be administered, e.g. in the form as it is marketed, e.g. under the trademark AREDIA. "Alendronic acid" can be administered, e.g., in the form as it is marketed, e.g. under the trademark FOSA-MAX. "Ibandronic acid" can be administered, e.g., in the form as it is marketed, e.g. under the trademark BONDRANAT. "Risedronic acid" can be administered, e.g., in the form as it is marketed, e.g. under the trademark ACTONEL. "Zoledronic acid" can be administered, e.g. in the form as it is marketed, e.g. under the trademark ZOMETA.

The term "mTOR inhibitors" relates to compounds which inhibit the mammalian target of rapamycin (mTOR) and which possess antiproliferative activity such as sirolimus (Rapamune™), everolimus (Certican™ or Afinitor™), CCI-779 and ABT578.

The term "heparanase inhibitor" as used herein refers to compounds which target, decrease or inhibit heparin sulfate degradation. The term includes, but is not limited to, PI-88.

The term "biological response modifier" as used herein refers to a lymphokine or interferons, e.g. interferon γ.

The term "inhibitor of Ras oncogenic isoforms", e.g. H-Ras, K-Ras, or N-Ras, as used herein refers to compounds which target, decrease or inhibit the oncogenic activity of Ras e.g. a "farnesyl transferase inhibitor" e.g. L-744832, DK8G557 or R115777 (Zarnestra).

The term "telomerase inhibitor" as used herein refers to compounds which target, decrease or inhibit the activity of telomerase. Compounds which target, decrease or inhibit the activity of telomerase are especially compounds which inhibit the telomerase receptor, e.g. telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase are e.g. bengamide or a derivative thereof.

The term "proteasome inhibitor" as used herein refers to compounds which target, decrease or inhibit the activity of the proteasome. Compounds which target, decrease or inhibit the activity of the proteasome include e.g. Bortezomid (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetrazolyle derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors e.g. compounds targeting, decreasing or inhibiting the activity of FMS-like tyrosine kinase receptors (Flt-3R); interferon, 1-b-D-arabino-furansylcytosine (ara-c) and bisulfan; and ALK inhibitors e.g. compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, e.g. PKC412, TKI258, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90 e.g., 17-ally-lamino, 17-demethoxygeldanamycin (17AAG), a geldanamycin derivative; other geldanamycin related compounds; radicicol and HDAC inhibitors. An example HSP90 inhibitor is AUY922.

The term "regulators of apoptosis" as used herein includes, but is not limited to, compounds targeting, decreasing or inhibiting the activity of Bcl2 family members (such as ABT-263) and IAP family members (such as AEG40826); or inducing apoptosis by known or unknown mechanism(s) of action (e.g. TRAIL antibody, DR5 antibody).

The term "antiproliferative antibodies" as used herein includes, but is not limited to, trastuzumab (Herceptin™), Trastuzumab-DM1, erbitux, bevacizumab (Avastin™) rituximab (Rituxan™), PRO64553 (anti-CD40), 2C4 Antibody and HCD122 antibody (anti-CD40). By antibodies is meant e.g. intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the formula (I) can be used in combination with standard leukemia therapies, especially in combination with therapies used for the treatment of AML. In particular, compounds of the formula (I) can be administered in combination with, e.g., farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The term "antileukemic compounds" includes, for example, Ara-C, a pyrimidine analog, which is the 2"-alpha-hydroxy ribose (arabinoside) derivative of deoxycytidine. Also included is the purine analog of hypoxanthine, 6-mercaptopurine (6-MP) and fludarabine phosphate.

Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A, LDH589 disclosed in WO 02/22577 and compounds disclosed in U.S. Pat. No. 6,552,065, in particular, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl) ethyl]-amino]methyl]phenyl]-2E-2-propenamide, or a pharmaceutically acceptable salt thereof, especially the lactate salt.

Somatostatin receptor antagonists as used herein refer to compounds which target, treat or inhibit the somatostatin receptor such as octreotide, and SOM230 (pasireotide).

Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives, such as PL-1, PL-2, PL-3, PL-4, PL-5, PL-6, PL-7 or PL-8 mentioned in Nandy et al., *Acta Oncologica*, Vol. 33, No. 8, pp. 953-961 (1994).

The term "S-adenosylmethionine decarboxylase inhibitors" as used herein includes, but is not limited to the compounds disclosed in U.S. Pat. No. 5,461,076.

Also included are in particular those compounds, proteins or monoclonal antibodies of VEGF disclosed in WO 98/35958, e.g. 1-(4-chloroanilino)-4-(4-pyridylmethyl)phthalazine or a pharmaceutically acceptable salt thereof, e.g. the succinate, or in WO 00/09495, WO 00/27820, WO 00/59509, WO 98/11223, WO 00/27819 and EP 0 769 947; those as described by Prewett et al, *Cancer Res*, Vol. 59, pp. 5209-5218 (1999); Yuan et al., *Proc Natl Acad Sci USA*, Vol. 93, pp. 14765-14770 (1996); Zhu et al., *Cancer Res*, Vol. 58, pp. 3209-3214 (1998); and Mordenti et al., *Toxicol Pathol*, Vol. 27, No. 1, pp. 14-21 (1999); in WO 00/37502 and WO 94/10202; ANGIOSTATIN, described by O'Reilly et al., *Cell*, Vol. 79, pp. 315-328 (1994); ENDOSTATIN, described by O'Reilly et al., *Cell*, Vol. 88, pp. 277-285 (1997); anthranilic acid amides; ZD4190; ZD6474; SU5416; SU6668; bevacizumab; or anti-VEGF antibodies or anti-VEGF receptor antibodies, e.g. rhuMAb and RHUFab, VEGF aptamer e.g. Macugon; FLT-4 inhibitors, FLT-3 inhibitors, VEGFR-2 IgG1 antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as e.g. VISUDYNE™ and porfimer sodium.

Angiostatic steroids as used herein refers to compounds which block or inhibit angiogenesis, such as, e.g., anecortave, triamcinolone. hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as e.g. fluocinolone, dexamethasone.

"Other chemotherapeutic compounds" include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code nos., generic or trade names may be taken from the actual edition of the standard compendium "The Merck Index" or from databases, e.g. Patents International (e.g. IMS World Publications).

None of the quotations of references made within the present disclosure is to be understood as an admission that the references cited are prior art that would negatively affect the patentability of the present invention.

The above-mentioned compounds, which can be used in combination with a compound of the formula (I), can be prepared and administered as described in the art, such as in the documents cited above.

A compound of the formula (I) can be administered alone or in combination with one or more other therapeutic compounds, possible combination therapy taking the form of fixed combinations or the administration of a compound of the invention and one or more other therapeutic (including prophylactic) compounds being staggered or given independently of one another, or the combined administration of fixed combinations and one or more other therapeutic compounds. A compound of the formula (I) can besides or in addition be administered especially for tumor therapy in combination with chemotherapy, radiotherapy, immunotherapy, photo therapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Compounds of particular interest as combinations partners as selected from the group of rapalogs such as RAD001, mTOR/PI3K inhibitors such as BEZ235, pan PI3K inhibitors such as BKM120, p110alpha inhibitors such as BYL719, anti-Notch mAb, CDK4 inhibitors such as LEE011, B-RAF inhibitors such as RAF265, MEK inhibitors, TNKS (Tankyrase) inhibitors, smoothened inhibitors such as LDE225, WNT inhibitors, c-Met inhibitors, PARP inhibitors, and Nilotinib.

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by inhibition of the MDM2/p53 and/or MDM4/p53 interaction. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by inhibition of the MDM2/p53 and/or MDM4/p53 interaction, wherein the medicament is prepared for administration with another therapeutic agent. The invention also provides the use of another therapeutic agent for treating a disease or condition mediated by inhibition of the MDM2/p53 and/or MDM4/p53 interaction, wherein the medicament is administered with a compound of formula (I).

The invention also provides a compound of formula (I) for use in a method of treating a disease or condition mediated by inhibition of the MDM2/p53 and/or MDM4/p53 interaction, wherein the compound of formula (I) is prepared for administration with another therapeutic agent. The invention also provides another therapeutic agent for use in a method of treating a disease or condition mediated by inhibition of the MDM2/p53 and/or MDM4/p53 interaction, wherein the other therapeutic agent is prepared for administration with a compound of formula (I). The invention also provides a compound of formula (I) for use in a method of treating a disease or condition mediated by inhibition of the MDM2/p53 and/or MDM4/p53 interaction, wherein the compound of formula (I) is administered with another therapeutic agent. The invention also provides another therapeutic agent for use in a method of treating a disease or condition mediated by inhibition of the MDM2/p53 and/or MDM4/p53 interaction, wherein the other therapeutic agent is administered with a compound of formula (I).

The invention also provides the use of a compound of formula (I) for treating a disease or condition mediated by inhibition of the MDM2/p53 and/or MDM4/p53 interaction, wherein the patient has previously (e.g. within 24 hours) been treated with another therapeutic agent. The invention also provides the use of another therapeutic agent for treating a disease or condition mediated by inhibition of the MDM2/p53 and/or MDM4/p53 interaction, wherein the patient has previously (e.g. within 24 hours) been treated with a compound of formula (I).

Typically, the compounds of formula (I) can be prepared according to the Schemes provided infra.

General synthesis scheme A:

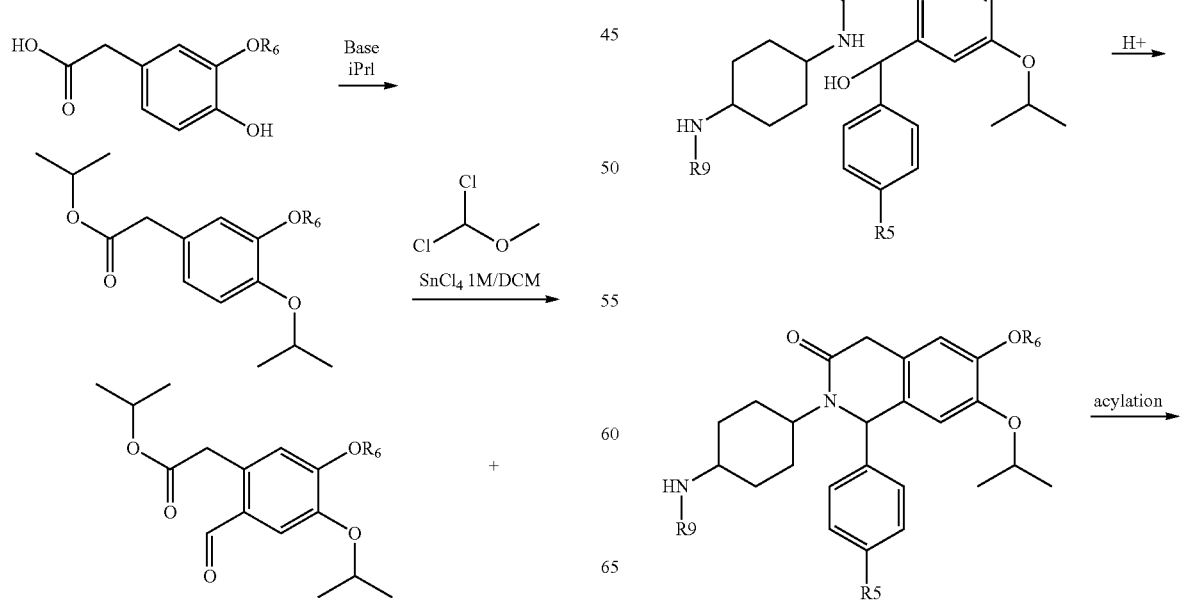

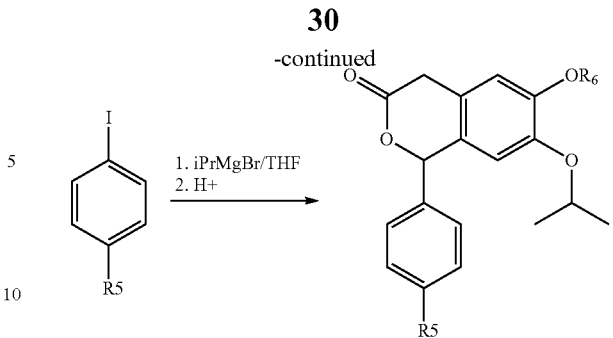

Scheme A illustrates the method of preparing intermediates (e.g. intermediate 1.2).

General synthesis scheme B:

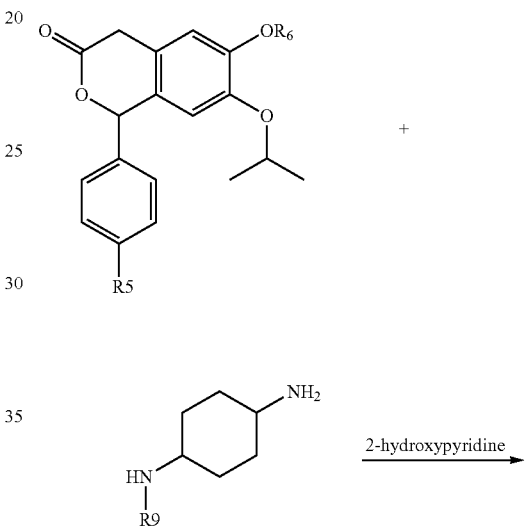

31
-continued
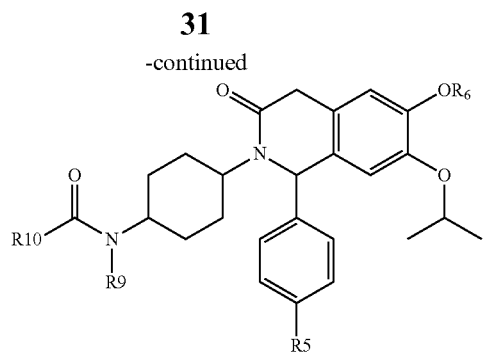
32
-continued
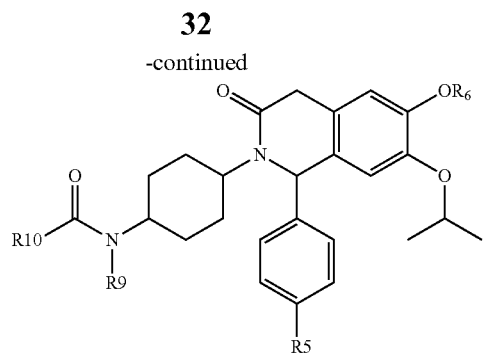
Scheme B illustrates the method of preparing compounds of the invention (e.g. example 2)
Scheme C illustrates the method of preparing compounds of the invention (e.g. example 10)
General synthesis scheme C:
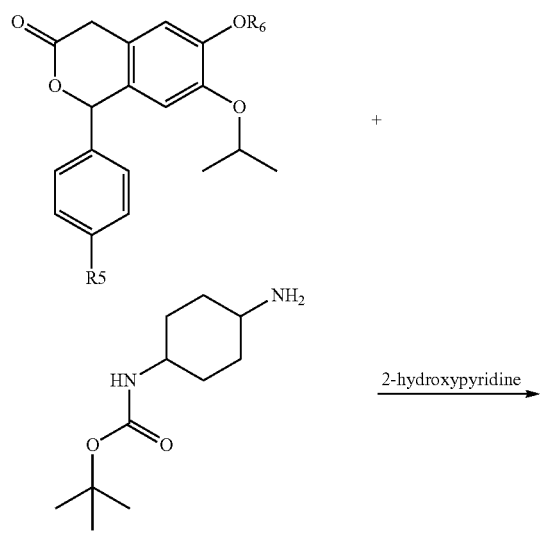
General synthesis scheme C:
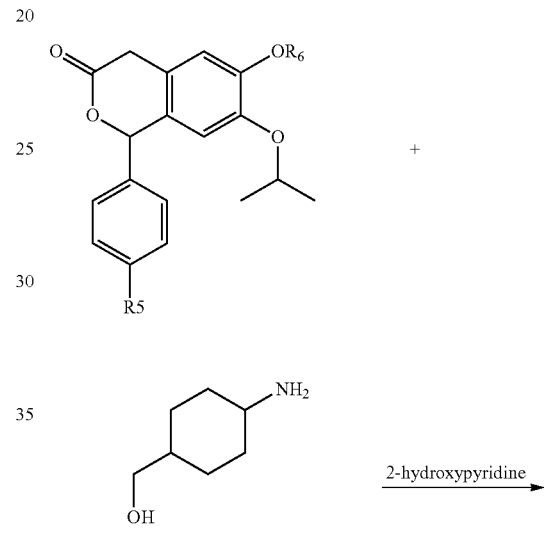
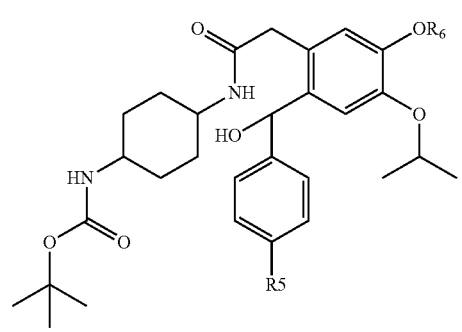
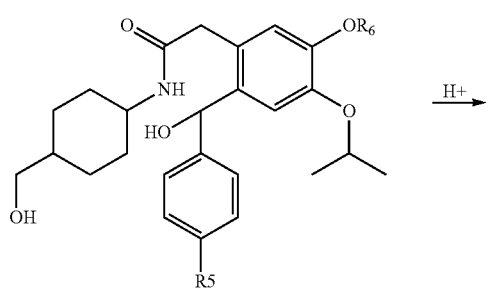
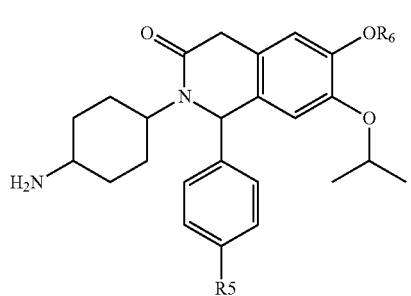
reductive amination acylation →
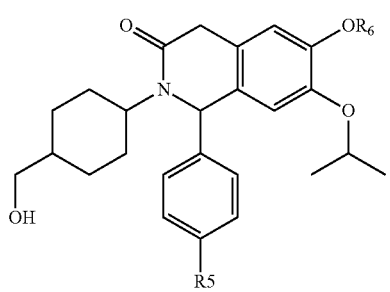
oxydation →

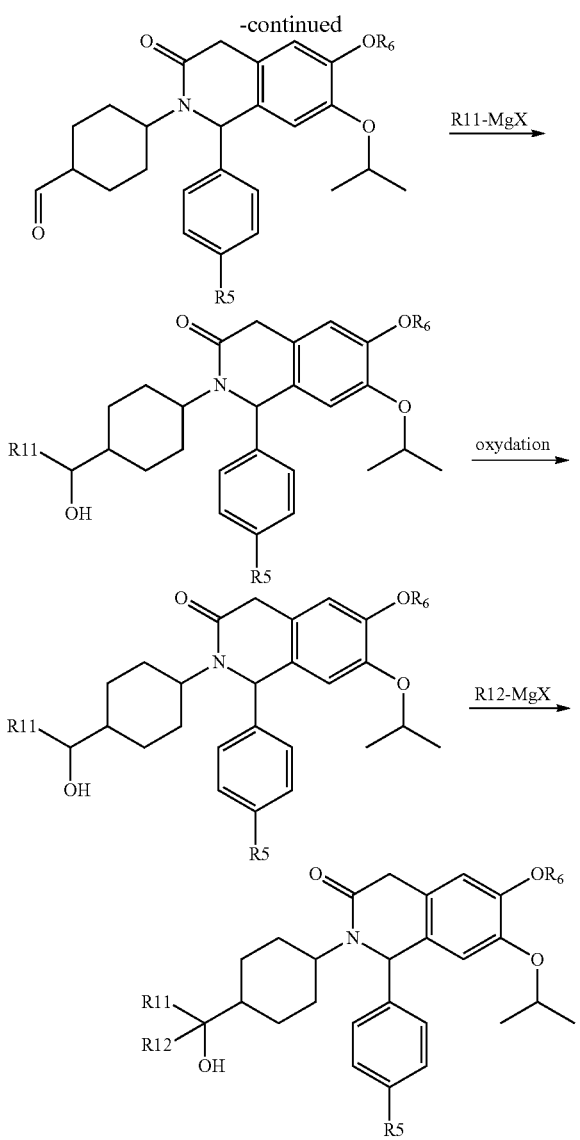

Scheme D illustrates the method of preparing compounds of the invention (e.g. example 28)

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the invention and intermediates can also be converted into each other according to methods generally known to those skilled in the art.

General Analytical Methods.

$^1$H-NMR measurements were performed on a Varian Ultrashield™ 400 (400 MHz), Bruker Ultrashield™ 600 (600 MHz) spectrometer using or not trimethylsilane as an internal standard. Chemical shifts (d-values) are reported in ppm downfield from tetramethylsilane, spectra splitting pattern are designated as singulet (s), doublet (d), doublet doublet (dd), triplet (t), quadruplet (q), multiplet or more overlapping signals (m), broad signal (br). Solvents are given in parentheses.

prep-HPLC purifications were performed using optimized gradient elution (CH$_3$CN/water with 0.1% TFA) with a Waters HPLC prep-system equipped with a UV detector Waters 2487 Dual Absorbance Detector, a MS detector Waters micromassZQ, and a reversed phase column Sun-Fire™ Prep, C18 OBD, 100×30 mm, 5 µm, or 100×19 mm, 5 µm.

TLC were performed with precoated silica gel 60 F$_{254}$ glass plates (Merck, Darmstadt, Germany) using the respective named solvent systems. Visualization was generally done by UV light (254 nm).

LC-MS spectra were recorded on a Waters 2795 Alliance HT instrument with a Sunfire™ C18, 4.6×20 mm, 3.5 µm column, eluting with a linear gradient of 5 to 100% MeCN (+0.1% TFA) in water (+0.1% TFA) in 4 min with a flow rate of 3 ml/min at 45° C., with positive ion electrospray ionization (Micromass ZQ Detector).

HPLC retention times ($^{X_1}t_{Ret}$) were reported in min and were recorded using the following conditions:

Retention times for system A ($^At_{Ret}$) were measured with a Thermo Finnigan instrument equipped with an UV 6000LP Photodiode Array Detector (DAD detection at 218 nm), eluting with an isocratic from 0-8.0 min of 2 to 100% MeCN (0.1% HCOOH) in water (+0.1% HCOOH), 8.0-10.0 min. 100% MeCN (0.1% HCOOH) then 10.0-11.0 min of 100% to 2% MeCN (+0.1% HCOOH) with a flow rate of 2.0 ml/min at 30° C. The column was a Chromolith Performance RP-18e, 4.6×100 mm (Merck)

Retention times for system B ($^Bt_{Ret}$) were measured with a Agilent 1100 instrument equipped with an Agilent 1100 series Dioden Array Detector (DAD detection at 215 nm), eluting with an isocratic from 0-8.0 min of 2 to 100% MeCN (0.1% TFA) in water (+0.1% TFA), 8.0-10.0 min. 100% MeCN (0.1% TFA), 10.0-11.0 min of 100% to 2% MeCN (+0.1 TFA) then 11.0-13.0 min of 2% MeCN (+0.1% TFA) with a flow rate of 2.0 ml/min at 25° C. The column was a Chromolith Performance RP-18e, 4.6×100 mm (Merck)

EXAMPLES

The following examples serve to illustrate the invention without limiting the scope thereof. Note that in some cases compounds mentioned as intermediates are also compounds of the formula I according to the invention (it is then mentioned that the compounds fall under formula I). Names of each examples or intermediates were automatically generated using AutoNom 2000 from IsisDraw. Where no specific source is indicated, starting materials and solvents are obtainable from customary suppliers, such as Sigma-Aldrich, Fluka, Alfa Aesar, Merck, or from providers indicated specifically. All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

Temperatures are given in degrees centigrade. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.
Abbreviations
EtOAc ethyl acetate
AcOH acetic acid
aq. aqueous
API-MS Atmospheric Pressure Ionization Mass Spectroscopy
brine saturated aqueous sodium chloride solution at RT
$^t$Bu t-butyl
$CDCl_3$ deuteriated chloroform
$CD_3OD$ deuteriated methanol
Celite trademark of Celite Corp. (World Minerals Inc.), Santa Barbara, Calif., USA, for filtering aid based on kieselguhr
$CHCl_3$ chloroform
conc. concentrated
$Cs_2CO_3$ cesium carbonate
DCM dichloromethane
DIPEA diisopropylethylamine
DME 1,2-dimethoxyethane
DMF N,N-dimethylformamide
DMSO dimethylsulfoxide
equiv. equivalent
Et ethyl
$Et_3N$ triethylamine
$Et_2O$ diethyl ether
EtOH ethanol
g gramm(s)
h hour(s)
HCl hydrogen chloride
HPLC high-pressure liquid chromatography
$H_2SO_4$ sulfuric acid
iPr isopropyl
$K_2CO_3$ potassium carbonate
KOH potassium hydroxide
$K_3PO_4$ potassium phosphate
LC-MS liquid chromatography mass spectroscopy
$LiBH_4$ lithium borohydride
LiOH lithium hydroxide
M molar
Me methyl
MeCN acetonitrile
mg milligram(s)
MeI methyl iodide
MeOH methanol
min minute(s)
ml or mL milliliter(s)
mmol millimole(s)
$MnO_2$ manganese(IV) oxide
MS mass spectrometry
$NaBH_4$ sodium borohydride
$NaBH_3CN$ sodium cyanoborohydride
$NaBH(OAc)_3$ sodium triacetoxyborohydride
$Na_2CO_3$ sodium carbonate
NaH sodium hydride
$NaHCO_3$ sodium bicarbonate
NaOH sodium hydroxide
$Na_2SO_4$ sodium sulfate
$NH_3$ ammoniac
$NH_4Cl$ ammonium chloride
NMM 4-methylmorpholine
NMR nuclear magnetic resonance
prep-HPLC preparative high-pressure liquid chromatography
quant. quantitative
$R_F$ retention factor
RT room temperature
$SiO_2$ silica
TBME tert-butyl-dimethyl ether
TFA trifluoroacetic acid
THF tetrahydrofurane
TLC thin layer chromatography
$t_{Ret}$ retention time Example 1

1-(4-Chloro-phenyl)-2-cyclohexyl-7-isopropoxy-6-methoxy-1,4-dihydro-2H-isoquinolin-3-one

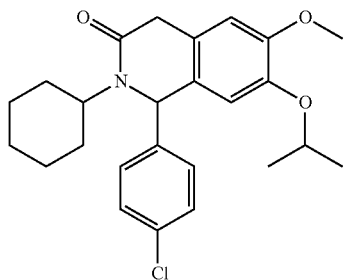 [SMILES: COc1cc2c(cc1OC(C)C)C(c1ccc(Cl)cc1)N(C1CCCCC1)C(=O)C2]

To a stirred solution of Intermediate 1.1 (0.200 g, 0.448 mmol) and AcOH (5.0 ml) was added $H_2SO_4$ 97% (0.035 ml, 0.628 mmol). The solution was stirred for 2 h at 100° C. The reaction mixture was concentrated in vacuo. The residue was neutralized with 1M $K_2CO_3$ and extracted with EtOAc (2×). The organic phases were washed with brine and dried over $Na_2SO_4$, filtered and evaporated to dryness. Purification of the residue by normal phase column chromatography, eluting with EtOAc-n-hexane, gave the title compound as a white foam (100 mg, 0.234 mmol, 52%). HPLC: $^A t_{Ret}$=6.50; LC-MS: m/z 428.3 [M+H]$^+$. $^1$H NMR (600 MHz, DMSO-d$_6$): 0.88-1.74 (m, 10H, 1.23-1.28 (q, 6H), 3.50 (dd, 2H), 3.68 (s, 3H), 4.35 (m, 1H), 4.50 (m, 1H), 5.89 (s, 1H), 6.75 (s, 1H), 7.25 (s, 1H), 7.39 (dd, 4H)

Intermediate 1.1: 2-{2-[(4-Chloro-phenyl)-hydroxy-methyl]-4-isopropoxy-5-methoxy-phenyl}-N-cyclohexyl-acetamide

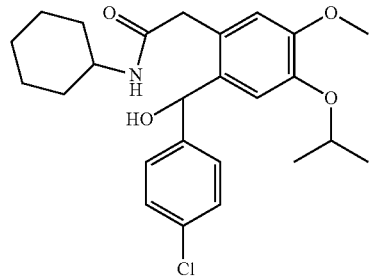 [SMILES: COc1cc(CC(=O)NC2CCCCC2)c(C(O)c2ccc(Cl)cc2)cc1OC(C)C]

To a stirred mixture of Intermediate 1.2 (0.200 g, 0.577 mmol) in triethylamine (4.0 ml) was added cyclohexylamine (0.330 ml, 2.88 mmol) and 2-hydroxy pyridine (0.055 g, 0.577 mmol). The mixture was stirred for 2 h at 80° C. The cooled reaction mixture was extracted between EtOAc (2×) and 1M aqueous NaHCO3 (1×). The organic phases were washed with brine and dried over $Na_2SO_4$, filtered and evaporated to dryness. The purification of the residue by recrystallization (EtOAc) gave the title compound as a beige solid (243 mg, 0.545 mmol, 94%). HPLC: $^{A}t_{Ret}$=6.04 min; LC-MS: m/z 891.5 [2M+H]$^{+}$;]$^{+}$; $^{1}$H NMR (600 MHz, DMSO-d$_{6}$):

0.88-1.72 (m, 10H), 1.11-1.17 (q, 6H), 3.36 (s, 2H), 3.46 (m, 1H), 3.68 (s, 3H), 4.30 (m, 1H), 5.88 (d, 1H), 5.89 (d, 1H), 6.71 (s, 1H), 6.79 (s, 1H), 7.30 (dd, 4H), 7.88 (d, 1H)

Intermediate 1.2: 1-(4-Chloro-phenyl)-7-isopropoxy-6-methoxy-isochroman-3-one

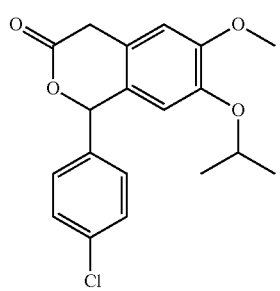 [SMILES: COc1cc2c(cc1OC(C)C)C(c1ccc(Cl)cc1)OC(=O)C2]

Reaction Vessel 1:

To a stirred solution of 1-chloro-4-iodobenzene (18.53 g, 77 mmol) in THF (90 ml) was added dropwise isopropylmagnesium chloride 2M in diethyl ether (38.5 ml, 77 mmol) during 15 min at −30° C. Stirring was continued for 1 h at −30° C. to get the "Grignard-Solution"

Reaction Vessel 2:

To a stirred solution of Intermediate 1.3 (18.3 g, 61.6 mmol) in THF (123 ml) was added the freshly prepared "Grignard-Solution" from reaction vessel 1 during 5 min at −30° C. Stirring was continued for 15 min at −30° C. and then quenched with 1M NH$_{4}$Cl (250 ml). The mixture was extracted with EtOAc (2×200 ml). The organic phases were washed with brine and dried over Na$_{2}$SO$_{4}$, filtered and evaporated to dryness. The residue was dissolved in DCM (308 ml) with stirring and TFA (0.237 ml, 3.1 mmol) was added. The solution was stirred for 18 h at RT. To the solution was added carefully 1M NaHCO$_{3}$ (250 ml) and then extracted with DCM (2×). The organic phases were washed with brine and dried over Na$_{2}$SO$_{4}$, filtered and evaporated. Purification of the residue by normal phase column chromatography, eluting with EtOAc-hexane 1:2, gave the title compound after crystallization (TBME) as a white solid (14.54 g, 41.5 mmol, 67%): HPLC: $^{B}t_{Ret}$=5.83 min; LC-MS: m/z 347.3 [M+H]$^{+}$; ]$^{+}$; $^{1}$H NMR (600 MHz, DMSO-d$_{6}$): 1.13-1.16 (q, 6H), 3.60 (d, 1H), 3.76 (s, 3H), 3.82 (d, 1H), 4.30 (m, 1H), 6.45 (s, 1H), 6.55 (s, 1H), 7.00 (s, 1H), 7.32-7.52 (dd, 4H)

Intermediate 1.3: (2-Formyl-4-isopropoxy-5-methoxy-phenyl)-acetic acid isopropyl ester

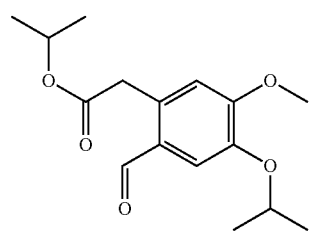 [SMILES: COc1cc(CC(=O)OC(C)C)c(C=O)cc1OC(C)C]

To a stirred solution of Intermediate 1.4 (31.0 g, 115 mmol), dichloro (methoxy)methan (20.86 ml, 230 mmol) in DCM (825 ml) was added dropwise SnCl$_{4}$(1M in DCM) (230 ml, 230 mmol) at 0-5° C. during 1 h. Stirring was continued for 1 h at 0° C. The reaction mixture was carefully poured into water (1.5 L) with stirring. The mixture was neutralized with solid NaHCO$_{3}$ and then extracted with DCM (3×). The organic phases were washed with brine and dried over Na$_{2}$SO$_{4}$, filtered and evaporated. Purification of the residue by normal phase column chromatography, eluting with EtOAc-hexane 1:5, gave the title compound after crystallization (diisopropyl ether-hexane) as a white solid (18.4 g, 61.9 mmol, 54%):

HPLC: $^{B}t_{Ret}$=5.18 min; LC-MS: m/z 295.1 [M+H]$^{+}$;]$^{+}$; $^{1}$H NMR (400 MHz, DMSO-d$_{6}$): 1.16-1.27 (dd, 12H), 3.82 (s, 3H), 3.95 (s, 2H), 4.60 (m, 1H), 4.86 (m, 1H), 7.00 (s, 1H), 7.43 (s, 1H), 9.91 (s, 1H)

Intermediate 1.4: (4-Isopropoxy-3-methoxy-phenyl)-acetic acid isopropyl ester

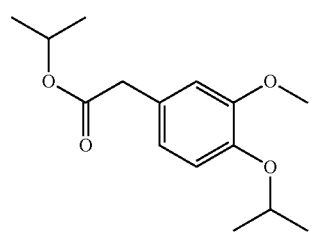 [SMILES: COc1cc(CC(=O)OC(C)C)ccc1OC(C)C]

To the stirred solution of (4-hydroxy-3-methoxy-phenyl)-acetic acid (24.9 g, 137 mmol) in DMF (274 ml) was added K$_{2}$CO$_{3}$ (56.7 g, 410 mmol) and 2-iodo-propane (34.2 ml, 342 mmol). The suspension was stirred for 3 h at 60° C. The cooled reaction mixture was concentrated and the residue was extracted between EtOAc (2×) and water (3×). The organic phases were washed with brine and dried over Na$_{2}$SO$_{4}$, filtered and evaporated. Purification of the residue by normal phase column chromatography, eluting with EtOAc-hexane 1:5, gave the title compound as a beige oil (27.0 g, 100 mmol, 73%): HPLC: $^{B}t_{Ret}$=5.59 min; $^{1}$H NMR (400 MHz, DMSO-d$_6$): 1.20-1.22 (dd, 12H), 3.50 (s, 2H), 3.70 (s, 3H), 4.46 (m, 1H), 4.87 (m, 1H), 6.71 (d, 1H), 6.85 (m, 2H)

Example 2

N-{4-[1-(4-Chloro-phenyl)-7-isopropoxy-6-methoxy-3-oxo-3,4-dihydro-1H-isoquinolin-2-yl]-cyclohexyl}-N-methyl-acetamide

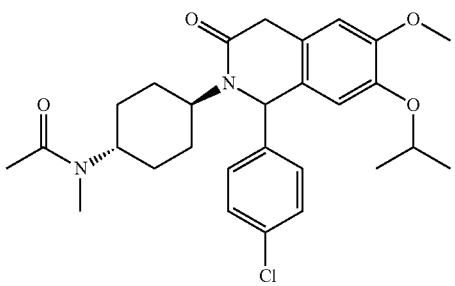 [SMILES: COc1cc2c(cc1OC(C)C)C(c1ccc(Cl)cc1)N([C@H]1CC[C@H](N(C)C(C)=O)CC1)C(=O)C2]

To the stirred solution of Intermediate 2.1 (0.083 g, 0.143 mmol) in DCM (1.43 ml) was added subsequently pyridine (0.017 ml, 0.215 mmol) and acetic anhydride (0.017 ml, 0.172 mmol) at 0° C. The reaction mixture was stirred for 30 min at 0° C. then quenched with 1M NaHCO$_3$ (40 ml) and extracted with EtOAc (2×). The organic phases were washed with brine and dried over Na$_2$SO$_4$, filtered and evaporated. Purification of the residue by normal phase column chromatography, eluting with DCM-MeOH 20:1, gave the title compound after crystallization (diisopropylether) as a white solid (51 mg, 0.101 mmol, 70%): HPLC: $^B$t$_{Ret}$=5.47; LC-MS: m/z 499.4 [M+H]$^+$. $^1$H NMR (600 MHz, DMSO-d$_6$): 1.20-1.91 (m, 8H), 1.23-1.28 (m, 6H), 1.95 and 2.00 (s (rotameres), 3H), 2.65 and 2.77 (s (rotameres), 3H), 3.51 (dd, 2H), 3.68 (s, 3H), 3.56 and 4.23 (m (rotameres), 1H), 4.39 (m, 1H), 4.49 (m, 1H), 5.90 and 5.95 (s (rotameres), 1H), 6.75 and 6.75 (s (rotameres), 1H), 7.22 (s, 1H), 7.35-7.43 (m, 4H)

Intermediate 2.1: 1-(4-Chloro-phenyl)-7-isopropoxy-6-methoxy-2-(4-methylamino-cyclohexyl)-1,4-dihydro-2H-isoquinolin-3-one

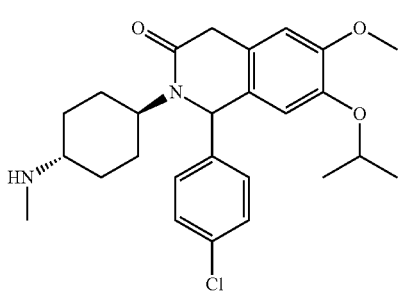 [SMILES: CN[C@H]1CC[C@H](N2C(=O)Cc3cc(OC)c(OC(C)C)cc3C2c2ccc(Cl)cc2)CC1]

The title intermediate (1.20 g, 2.64 mmol, 48%) was obtained as a slightly yellow foam from Intermediate 2.2 (2.60 g, 5.47 mmol) analogously to Example 1; HPLC: $^A$t$_{Ret}$=4.61 min; LC-MS: m/z 457.1 [M+H]$^+$. $^1$H NMR (400 MHz, DMSO-d$_6$): 0.98 (m, 2H), 1.20-1.25 (q, 6H), 1.37-1.49 (m, 2H), 1.68-1.89 (m, 4H), 2.12 (m, 1H), 2.20 (s, 3H), 3.30 (H$_2$O and NH, 1H), 3.48 (dd, 2H), 3.66 (s, 3H), 4.28 (m, 1H), 4.47 (m, 1H), 5.84 (s, 1H), 6.72 (s, 1H), 7.18 (s, 1H), 7.35 (dd, 4H)

Intermediate 2.2: 2-{2-[(4-Chloro-phenyl)-hydroxymethyl]-4-isopropoxy-5-methoxy-phenyl}-N-(4-methylamino-cyclohexyl)-acetamide

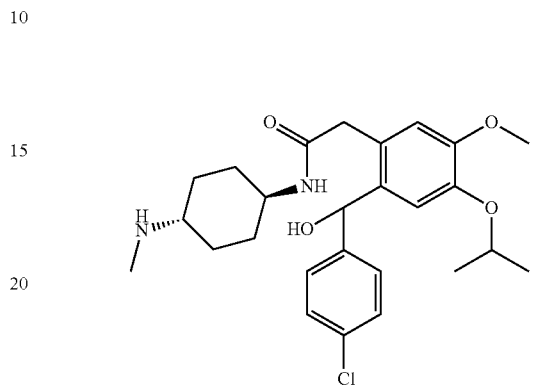

To the stirred mixture of Intermediate 1.2 (0.900 g, 2.57 mmol) in triethylamine (17.9 ml) was added (trans)-N-methyl-cyclohexane-1,4-diamine (1.83 g, 12.85 mmol) and 2-hydroxy pyridine (0.244 g, 2.57 mmol). The mixture was stirred for 1 h at 80° C. The cooled reaction mixture was extracted between EtOAc (2×) and 1M aqueous NaHCO3 (1×). The organic phases were washed with brine and dried over Na$_2$SO$_4$, filtered and evaporated. Purification of the residue by normal phase column chromatography, eluting with DCM-MeOH-aq. ammonia 30% 40:10:1, gave the title compound (0.90 g, 1.876 mmol, 73%). HPLC: $^B$t$_{Ret}$=4.48 min; LC-MS: m/z 475.4 [M+H]$^+$; $^1$H NMR (600 MHz, DMSO-d$_6$): 1.01-1.89 (m, 8H), 1.13-1.19 (q, 6H), 2.30 (s, 3H), 2.33 (m, 1H), 3.30 (H$_2$O and NH(Me), 1H), 3.37 (s, 2H), 3.40 m, 1H), 3.69 (s, 3H), 4.32 (m, 1H), 5.88-5.93 (m, 2H), 6.73 (s, 1H), 6.79 (s, 1H), 7.32 (dd, 4H), 7.95 (d, 1H)

Intermediate 2.3:
(trans)-N-Methyl-cyclohexane-1,4-diamine

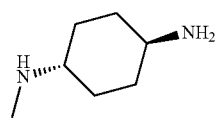

To the stirred solution of (trans)-(4-amino-cyclohexyl)-carbamic acid tert-butyl ester (4.29 g, 20.0 mmol) in THF (160 ml) (under argon atmosphere) was added LiAlH$_4$ (3.13 g, 80 mmol) in three portions, at 0-5° C. The suspension was heated to 70° C. and stirred for additional 18 h. The reaction mixture was cooled to 0° C. and then subsequently addition of THF-H$_2$O 1:1 (4 ml), 4M NaOH (8 ml) and water (12 ml). Stirring was continued for 3 h at RT. The white suspension was filtered (Celite) and the filtrate was concentrated in vacuo to get the crude title compound as a slightly yellow liquid. This material was used for the next step without further purifications.

Example 3

N-{4-[1-(4-Chloro-phenyl)-7-isopropoxy-6-methoxy-3-oxo-3,4-dihydro-1H-isoquinolin-2-yl]-cyclohexyl}-N-ethyl-acetamide

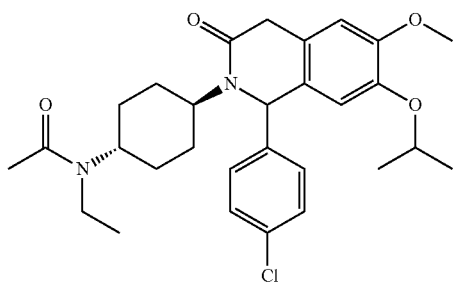 [SMILES: CCN(C(C)=O)[C@H]1CC[C@H](N2C(=O)Cc3cc(OC)c(OC(C)C)cc3C2c2ccc(Cl)cc2)CC1]

The title compound (26 mg, 0.051 mmol) was obtained as a white foam starting from Intermediate 1.2 and (trans)-N-ethyl-cyclohexane-1,4-diamine analogously to Example 2; HPLC: $^A t_{Ret}$=5.56; LC-MS: m/z 513.3 [M+H]$^+$.

Example 4

N-{4-[1-(4-Chloro-phenyl)-7-isopropoxy-6-methoxy-3-oxo-3,4-dihydro-1H-isoquinolin-2-yl]-cyclohexyl}-acetamide

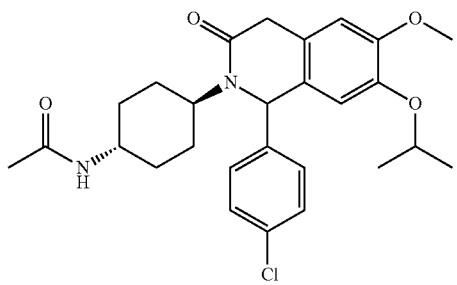 [SMILES: COc1cc2c(cc1OC(C)C)C(c1ccc(Cl)cc1)N([C@H]1CC[C@H](NC(C)=O)CC1)C(=O)C2]

The title compound (95 mg, 0.194 mmol, 87%) was obtained as a white solid (diisopropyl ether) from Intermediate 4.1 (100 mg, 0.223 mmol) analogously to Example 2; HPLC: $^B t_{Ret}$=5.19; LC-MS: m/z 485.4 [M+H]$^+$. $^1$H NMR (600 MHz, DMSO-d$_6$): 1.11-1.80 (m, 8H), 1.22-1.26 (q, 6H), 1.73 (s, 3H), 3.44 (m, 1H), 3.51 (dd, 2H), 3.67 (s, 3H), 4.33 (m, 1H), 4.48 (m, 1H), 5.91 (s, 1H), 6.74 (s, 1H), 7.18 (s, 1H), 7.36 (dd, 4H), 7.73 (d, 1H)

Intermediate 4.1: 2-(4-Amino-cyclohexyl)-1-(4-chloro-phenyl)-7-isopropoxy-6-methoxy-1,4-dihydro-2H-isoquinolin-3-one

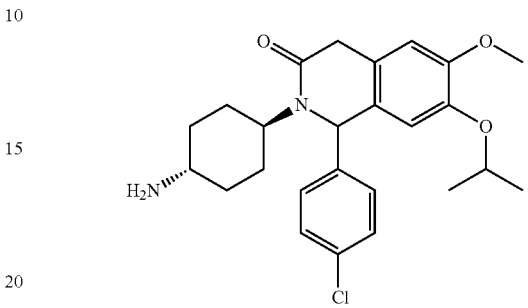

The title intermediate (0.708 g, 1.582 mmol, 45%) was obtained as a white foam from Intermediate 4.2 (1.95 g, 3.48 mmol) analogously to Example 1; HPLC: $^B t_{Ret}$=4.55; LC-MS: m/z 443.4 [M+H]$^+$. $^1$H NMR (600 MHz, DMSO-d$_6$): 0.92-1.78 (m, 8H), 1.20-1.25 (q, 6H), 2.42 (m, 1H), 3.30 (H$_2$O and NH$_2$, 2H), 3.47 (dd, 2H), 3.66 (s, 3H), 4.26 (m, 1H), 4.47 (m, 1H), 5.83 (s, 1H), 6.72 (s, 1H), 7.20 (s, 1H), 7.36 (dd, 4H)

Intermediate 4.2: [4-(2-{2-[(4-Chloro-phenyl)-hydroxy-methyl]-4-isopropoxy-5-methoxy-phenyl}-acetylamino)-cyclohexyl]-carbamic acid tert-butyl ester

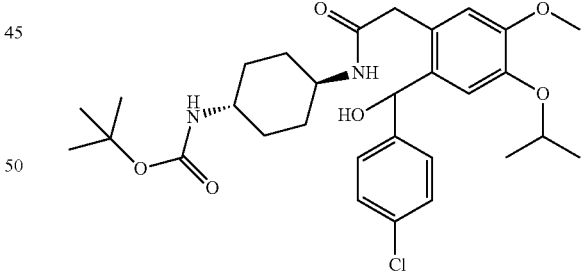

The title intermediate (0.538 g, 0.959 mmol, 96%) was obtained as a white solid (by crystallization in TBME) from Intermediate 1.2 (0.347 g, 1.00 mmol) and (trans)-(4-aminocyclohexyl)-carbamic acid tert-butyl ester (0.643 g, 3.0 mmol) analogously to Intermediate 2.2; HPLC: $^B t_{Ret}$=5.95 min; LC-MS: m/z 1123.6 [2M+H]$^+$; $^1$H NMR (600 MHz, DMSO-d$_6$): 1.12-1.20 (m, 4H), 1.15-1.20 (q, 6H), 1.37 (s, 9H), 1.69-1.76 (m, 4H), 3.17 (m, 1H), 3.37-3.39 (m, 3H), 3.70

(s, 3H), 4.33 (m, 1H), 5.90 (m, 2H), 6.73 (d, 1H), 6.74 (s, 1H), 6.80 (s, 1H), 7.32 (dd, 4H), 7.95 (d, 1H)

Example 5

1-(4-Chloro-phenyl)-2-{4-[(2-hydroxy-ethyl)-methyl-amino]-cyclohexyl}-7-isopropoxy-6-methoxy-1,4-dihydro-2H-isoquinolin-3-one

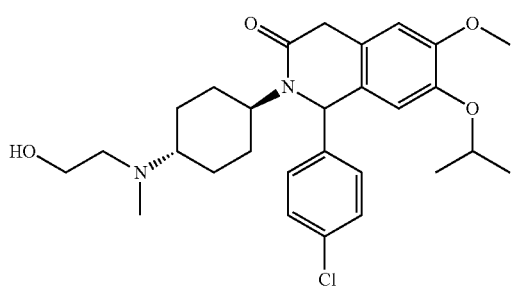 [SMILES: COc1cc2c(cc1OC(C)C)C(c1ccc(Cl)cc1)N([C@H]1CC[C@H](N(C)CCO)CC1)C(=O)C2]

To the stirred solution of Intermediate 2.1 (60 mg, 0.130 mmol) in DMF (1.3 ml) was added subsequently triethylamine (0.027 ml, 0.195 mmol) and [1,3,2]Dioxathiolane 2-oxide (0.012 ml, 0.156 mmol). The reaction mixture was stirred for 24 h at 80° C. Further triethylamine (0.027 ml, 0.195 mmol) and [1,3,2]dioxathiolane 2-oxide (0.012 ml, 0.156 mmol) were added and heating was continued for additional 2 days. The reaction mixture was extracted between 1M NaHCO$_3$ and EtOAc (2×). The organic phases were washed with brine and dried over Na$_2$SO$_4$, filtered and evaporated. Purification of the residue by normal phase column chromatography, eluting with DCM-MeOH-aq. ammonia 30% 200:10:1, gave the title compound as white foam (12 mg, 0.024 mmol, 18%): HPLC: $^B$t$_{Ret}$=4.61; LC-MS: m/z 501.4 [M+H]$^+$. $^1$H NMR (600 MHz, DMSO-d$_6$): 1.22-1.26 (q, 6H), 1.22-1.73 (m, 8H), 2.15 (s, 3H), 2.26 (m, 1H), 2.42 (m, 2H), 3.38 (m, 2H), 3.49 (dd, 2H), 3.67 (s, 3H), 4.29 (m, 2H), 4.48 (m, 1H), 5.86 (s, 1H), 6.73 (s, 1H), 7.20 (s, 1H), 7.36 (dd, 4H)

Example 6

{4-[1-(4-Chloro-phenyl)-7-isopropoxy-6-methoxy-3-oxo-3,4-dihydro-1H-isoquinolin-2-yl]-cyclohexyl}-urea

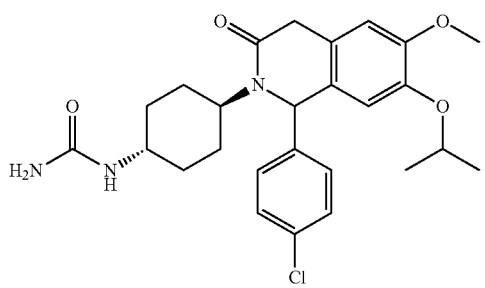 [SMILES: COc1cc2c(cc1OC(C)C)C(c1ccc(Cl)cc1)N([C@H]1CC[C@H](NC(N)=O)CC1)C(=O)C2]

To the stirred suspension of Intermediate 2.1 (45 mg, 0.10 mmol) and water (3.0 ml) was subsequently added 1M HCl (0.10 ml, 0.10 mmol) and potassium cyanate (25 mg, 0.30 mmol). The reaction mixture was stirred for 17 h at 50° C. The reaction mixture was extracted between 1M NaHCO$_3$ and EtOAc (2×). The organic phases were washed with brine and dried over Na$_2$SO$_4$, filtered and evaporated. Purification of the residue by normal phase column chromatography, eluting with DCM-MeOH-aq. ammonia 30% 40:10:1, gave the title compound as a white foam (32 mg, 0.065 mmol, 65%): HPLC: $^B$t$_{Ret}$=4.97; LC-MS: m/z 486.5 [M+H]$^+$. $^1$H NMR (600 MHz, DMSO-d$_6$): 1.05-1.82 (m, 8H), 1.22-1.26 (q, 6H), 3.22 (m, 1H), 3.50 (dd, 2H), 3.67 (s, 3H), 4.33 (m, 1H), 4.48 (m, 1H), 5.29 (s, 2H), 5.79 (d, 1H), 5.89 (s, 1H), 6.74 (s, 1H), 7.19 (s, 1H), 7.37 (dd, 4H)

Example 7

1-{4-[1-(4-Chloro-phenyl)-7-isopropoxy-6-methoxy-3-oxo-3,4-dihydro-1H-isoquinolin-2-yl]-cyclohexyl}-1-methyl-urea

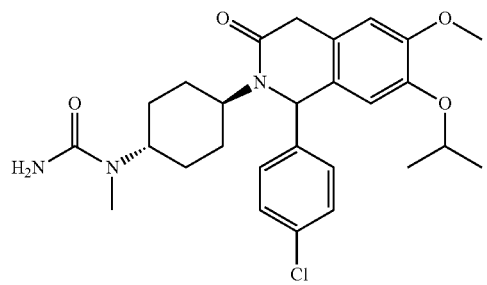 [SMILES: COc1cc2c(cc1OC(C)C)C(c1ccc(Cl)cc1)N([C@H]1CC[C@H](N(C)C(N)=O)CC1)C(=O)C2]

The title compound (0.041 g, 0.081 mmol, 81%) was obtained as a white foam from Intermediate 2.1 (0.046 g, 1.00 mmol) analogously to Example 6; HPLC: $^B$t$_{Ret}$=5.14; LC-MS: m/z 500.3 [M+H]$^+$.

Example 8

1-(4-Chloro-phenyl)-7-isopropoxy-6-methoxy-2-[4-(2-oxo-imidazolidin-1-yl)-cyclohexyl]-1,4-dihydro-2H-isoquinolin-3-one

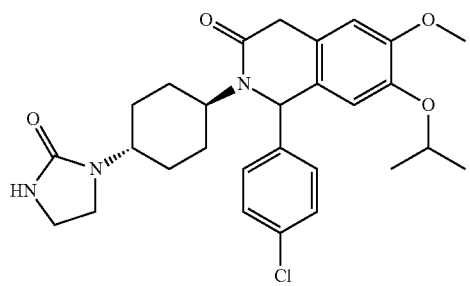 [SMILES: COc1cc2c(cc1OC(C)C)C(c1ccc(Cl)cc1)N([C@H]1CC[C@H](N3CCNC3=O)CC1)C(=O)C2]

To the stirred solution of Intermediate 8.1 (60 mg, 0.117 mmol) in THF (4.6 ml) was added 1'1-carbonyl-diimidazole (21.6 mg, 0.129 mmol). The mixture was heated to 65° C. and stirred for 40 min. The reaction mixture was extracted between 1M NaHCO$_3$ and EtOAc (2×). The organic phases were washed with brine and dried over Na$_2$SO$_4$, filtered and evaporated. Purification of the residue by normal phase column chromatography, eluting with DCM-MeOH-aq. ammonia 30% 200:20:1, gave the title compound as a white foam (15 mg, 0.029 mmol, 25%): HPLC: $^B t_{Ret}$=5.26; LC-MS: m/z 512.3 [M+H]$^+$.

Intermediate 8.1: 2-[4-(2-Amino-ethylamino)-cyclohexyl]-1-(4-chloro-phenyl)-7-isopropoxy-6-methoxy-1,4-dihydro-2H-isoquinolin-3-one

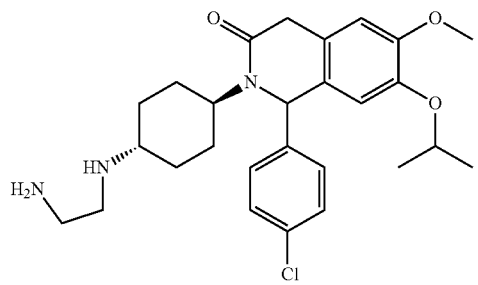 [SMILES: COc1cc2c(cc1OC(C)C)C(c1ccc(Cl)cc1)N([C@H]1CC[C@H](NCCN)CC1)C(=O)C2]

To the stirred solution of Intermediate 8.2 (75 mg, 0.127 mmol) in DCM (1.27 ml) was added TFA (0.195 ml, 2.53 mmol) at 0° C. and then stirred for 3.5 h at RT. The reaction mixture was extracted between 1M NaHCO$_3$ and EtOAc (2×). The organic phases were washed with brine and dried over Na$_2$SO$_4$, filtered and evaporated, affording the crude title compound as a yellow oil (60 mg, 0.117 mmol, 93%): HPLC: $^B t_{Ret}$=4.22; LC-MS: m/z 486.3 [M+H]$^+$.

Intermediate 8.2: (2-{4-[1-(4-Chloro-phenyl)-7-isopropoxy-6-methoxy-3-oxo-3,4-dihydro-1H-isoquinolin-2-yl]-cyclohexylamino}-ethyl)-carbamic acid tert-butyl ester

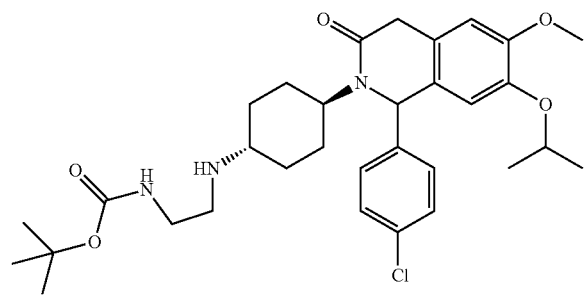 [SMILES: COc1cc2c(cc1OC(C)C)C(c1ccc(Cl)cc1)N([C@H]1CC[C@H](NCCNC(=O)OC(C)(C)C)CC1)C(=O)C2]

To the stirred solution of Intermediate 4.1 (148 mg, 0.330 mmol) in MeOH (6.60 ml) was added (2-oxo-ethyl)-carbamic acid tert-butyl ester [CAS 89711-08-0] (84 mg, 0.396 mmol) at RT. After 10 min, sodium NaBH$_3$CN (32.7 mg, 0.494 mmol) was added and stirring was continued for 20 h at RT. The reaction mixture was extracted between 1M NaHCO$_3$ and EtOAc (2×). The organic phases were washed with brine and dried over Na$_2$SO$_4$, filtered and evaporated. Purification of the residue by normal phase column chromatography, eluting with DCM-MeOH-aq. ammonia 30% 200:20:1, gave the title compound as a white foam (78 mg, 0.132 mmol, 40%): HPLC: $^B t_{Ret}$=5.16; LC-MS: m/z 586.4 [M+H]$^+$.

Example 9

N-{4-[1-(4-Chloro-phenyl)-7-isopropoxy-6-methoxy-3-oxo-3,4-dihydro-1H-isoquinolin-2-yl]-cyclohexyl}-3-hydroxy-N-methyl-propionamide

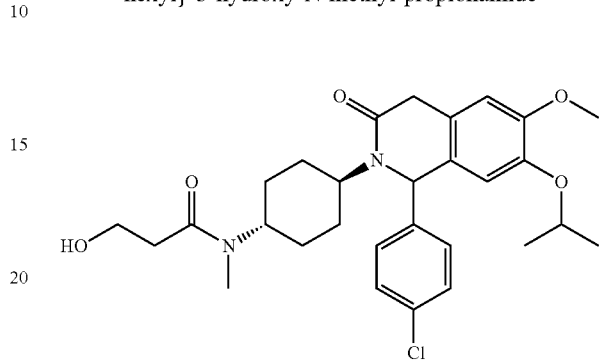

To the stirred solution of Intermediate 9.1 (86 mg, 0.154 mmol) in THF (1.0 ml) was added LiBH$_4$ (10.1 mg, 0.463 mmol) at RT. Stirring was continued for 3 h. The reaction mixture was extracted between 1M NaHCO$_3$ and EtOAc (2×). The organic phases were washed with brine and dried over Na$_2$SO$_4$, filtered and evaporated. Purification of the residue by normal phase column chromatography, eluting with DCM-MeOH 19:1, gave the title compound as a white foam (57 mg, 0.107 mmol, 69%): HPLC: $^A t_{Ret}$=4.99; LC-MS: m/z 529.3 [M+H]$^+$.

Intermediate 9.1: N-{4-[1-(4-Chloro-phenyl)-7-isopropoxy-6-methoxy-3-oxo-3,4-dihydro-1H-isoquinolin-2-yl]-cyclohexyl}-N-methyl-malonamic acid methyl ester

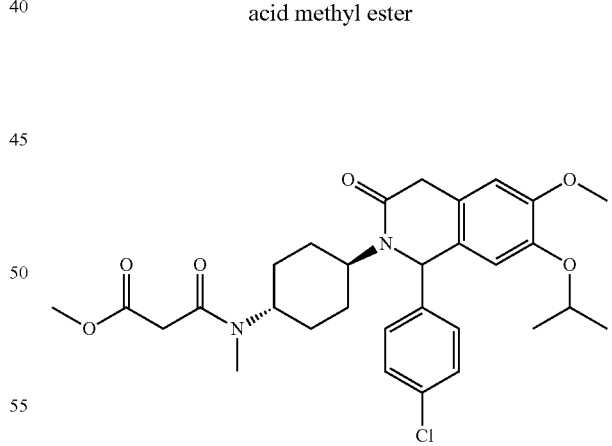

To the stirred mixture of MeOH-THF 3:2 (4 ml) was added subsequently NaBH$_4$ (23.85 mg, 0.630 mmol) and LiCl (26.7 mg, 0.630 mmol) at RT. Stirring was continued for 45 min and then the solution of Intermediate 9.2 (90 mg, 0.158 mmol) in MeOH-THF 3:2 (1 ml) was added. Stirring was continued for 36 h at RT. The reaction mixture was extracted between 1M NaHCO$_3$ and EtOAc (2×). The organic phases were washed with brine and dried over Na$_2$SO$_4$, filtered and evaporated, affording the crude title compound as a white foam (84 mg, 0.149 mmol, 95%): HPLC: $^A t_{Ret}$=5.45; LC-MS: m/z 557.3 [M+H]⁺.

Intermediate 9.2: N-{4-[1-(4-Chloro-phenyl)-7-isopropoxy-6-methoxy-3-oxo-3,4-dihydro-1H-isoquinolin-2-yl]-cyclohexyl}-N-methyl-malonamic acid ethyl ester

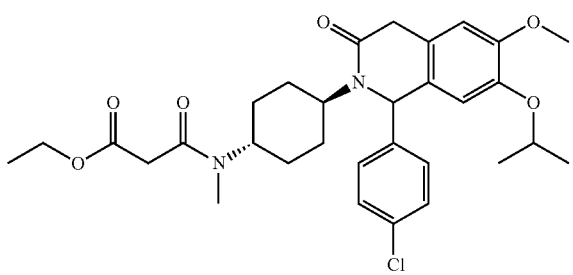 [SMILES: CCOC(=O)CC(=O)N(C)[C@H]1CC[C@H](N2C(=O)Cc3cc(OC)c(OC(C)C)cc3C2c2ccc(Cl)cc2)CC1]

To the stirred solution of Intermediate 2.1 (0.100 g, 0.219 mmol) in DCM (5.0 ml) was added subsequently triethylamine (0.091 ml, 0.656 mmol) and chlorocarbonyl acetic acid ethyl ester (0.033 ml, 0.263 mmol) at RT. The reaction mixture was stirred for 2 h at RT, then quenched with 1M NaHCO₃ and extracted with EtOAc (2×). The organic phases were washed with brine and dried over Na₂SO₄, filtered and evaporated. Purification of the residue by normal phase column chromatography, eluting with DCM-MeOH 19:1, gave the title compound as a white foam (98 mg, 0.168 mmol, 77%): HPLC: $^A t_{Ret}$=5.66; LC-MS: m/z 571.3 [M+H]⁺.

Example 10

N-{4-[1-(4-Chloro-phenyl)-7-isopropoxy-6-methoxy-3-oxo-3,4-dihydro-1H-isoquinolin-2-yl]-cyclohexyl}-N-propyl-acetamide

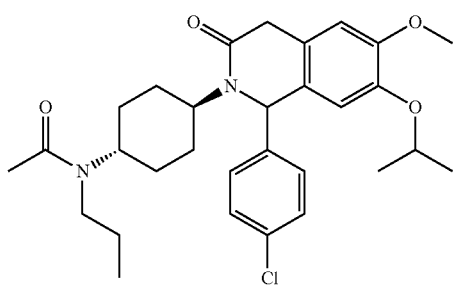 [SMILES: CCCN(C(C)=O)[C@H]1CC[C@H](N2C(=O)Cc3cc(OC)c(OC(C)C)cc3C2c2ccc(Cl)cc2)CC1]

The title compound (7.0 mg, 0.013 mmol, 79%) was obtained as a white foam from Intermediate 10.1 (8.0 mg, 0.016 mmol) analogously to Example 2; HPLC: $^A t_{Ret}$=5.87; LC-MS: m/z 527.3 [M+H]⁺.

Intermediate 10.1: 1-(4-Chloro-phenyl)-7-isopropoxy-6-methoxy-2-(4-propylamino-cyclohexyl)-1,4-dihydro-2H-isoquinolin-3-one

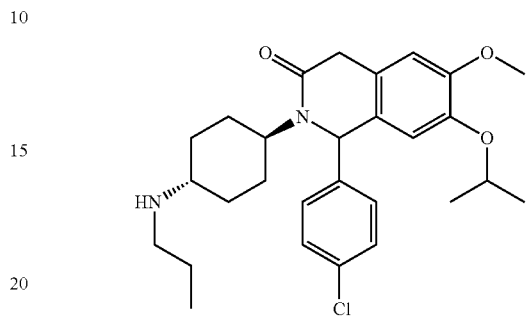

To the stirred solution of Intermediate 4.1 (100 mg, 0.226 mmol) in DCM (4.0 ml) was added subsequently propionaldehyde (0.017 ml, 0.226 mmol), triethylamine (0.031 ml, 0.226 mmol) and molecular sieve 4A (100 mg) and stirring was continued for 0.5 h at RT. The reaction mixture was cooled to 0° C. and sodium triacetoxyborohydride (91 mg, 0.429 mmol) was added. The reaction mixture was stirred for 2 h at 0° C., then quenched with 1M NaHCO₃ and extracted with DCM (2×). The organic phases were washed with brine and dried over Na₂SO₄, filtered and evaporated. Purification of the residue by normal phase column chromatography, eluting with DCM-MeOH-aq. ammonia 30% 40:10:1, gave the title compound as a white foam (65 mg, 0.134 mmol, 59%): HPLC: $^A t_{Ret}$=4.49; LC-MS: m/z 485.3 [M+H]⁺.

Example 11

N-{4-[1-(4-Chloro-phenyl)-7-isopropoxy-6-methoxy-3-oxo-3,4-dihydro-1H-isoquinolin-2-yl]-cyclohexyl}-N-propyl-formamide

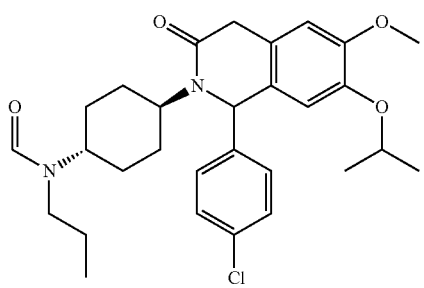 [SMILES: CCCN(C=O)[C@H]1CC[C@H](N2C(=O)Cc3cc(OC)c(OC(C)C)cc3C2c2ccc(Cl)cc2)CC1]

The mixture of Intermediate 10.1 (30 mg, 0.062 mmol) and ethyl formate (2.00 ml, 12.37 mmol) was stirred for 3 days at 50° C. Purification of the crude reaction mixture by normal phase column chromatography, eluting with DCM-MeOH-aq. ammonia 30% 200:20:1, gave the title compound as a white foam (26 mg, 0.051 mmol, 82%): HPLC: $^A t_{Ret}$=5.79; LC-MS: m/z 513.4 [M+H]⁺.

Examples: 12, 13 and 14 were obtained analogously to Example 10 by the reaction of Intermediate 4.1 with the corresponding aldehydes or ketones.

| | Structure | Name/HPLC/MS |
|---|---|---|
| 12 | 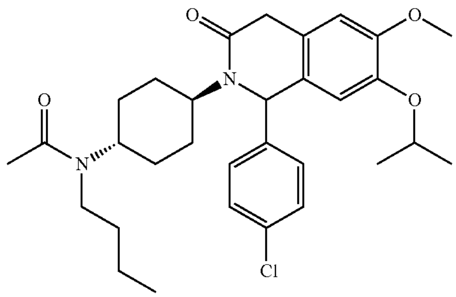 [SMILES: CCCCN(C(C)=O)[C@H]1CC[C@H](N2C(=O)Cc3cc(OC)c(OC(C)C)cc3C2c2ccc(Cl)cc2)CC1] | N-Butyl-N-{4-[1-(4-chloro-phenyl)-7-isopropoxy-6-methoxy-3-oxo-3,4-dihydro-1H-isoquinolin-2-yl]-cyclohexyl}-acetamide<br>HPLC: $^{A}t_{Ret}$ = 6.13; LC-MS: m/z 541.3 [M + H]$^+$. |
| 13 | 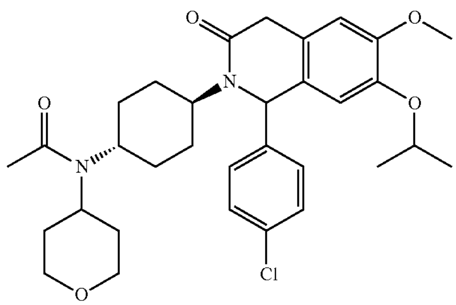 [SMILES: COc1cc2c(cc1OC(C)C)C(c1ccc(Cl)cc1)N([C@H]1CC[C@H](N(C(C)=O)C3CCOCC3)CC1)C(=O)C2] | N-{4-[1-(4-Chloro-phenyl)-7-isopropoxy-6-methoxy-3-oxo-3,4-dihydro-1H-isoquinolin-2-yl]-cyclohexyl}-N-(tetrahydro-pyran-4-yl)-acetamide<br>HPLC: $^{A}t_{Ret}$ = 5.63; LC-MS: m/z 569.3 [M + H]$^+$. |
| 14 | 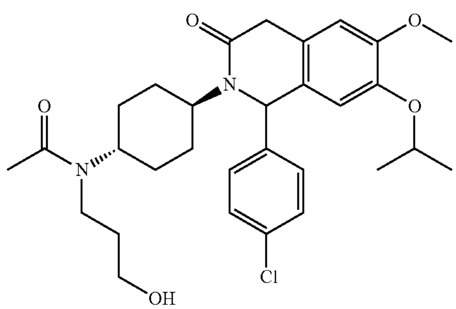 [SMILES: COc1cc2c(cc1OC(C)C)C(c1ccc(Cl)cc1)N([C@H]1CC[C@H](N(CCCO)C(C)=O)CC1)C(=O)C2] | N-{4-[1-(4-Chloro-phenyl)-7-isopropoxy-6-methoxy-3-oxo-3,4-dihydro-1H-isoquinolin-2-yl]-cyclohexyl}-N-(3-hydroxy-propyl)-acetamide<br>HPLC: $^{A}t_{Ret}$ = 5.12; LC-MS: m/z 543.3 [M + H]$^+$. |

Example 15

2-(4-Acetyl-cyclohexyl)-1-(4-chloro-phenyl)-7-isopropoxy-6-methoxy-1,4-dihydro-2H-isoquinolin-3-one

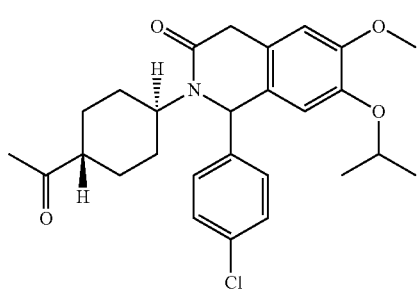 [SMILES: COc1cc2c(cc1OC(C)C)C(c1ccc(Cl)cc1)N([C@H]1CC[C@H](C(C)=O)CC1)C(=O)C2]

To the stirred solution of Intermediate 15.1 (0.051 g, 0.10 mmol) in DMSO (1.0 ml) was added triethylamine (0.042 ml, 0.30 mmol). The mixture is cooled to 10° C. and sulfur trioxyde pyridine complex (0.048 mg, 0.30 mmol) was added. The mixture was stirred for 3 h at RT. The reaction mixture was poured into 1M citric acid and extracted with EtOAc (2×). The organic phases were washed with 1M citric acid, water, 1M NaHCO$_3$, brine and dried over Na$_2$SO$_4$, filtered and evaporated. Purification of the residue by normal phase column chromatography, eluting with EtOAc-heptane 3:1, gave the title compound as a white foam (23 mg, 0.048 mmol, 48%): HPLC: $^{B}t_{Ret}$=5.75; LC-MS: m/z 470.4 [M+H]$^+$.

Intermediate 15.1: 1-(4-Chloro-phenyl)-2-[4-(1-hydroxy-ethyl)-cyclohexyl]-7-isopropoxy-6-methoxy-1,4-dihydro-2H-isoquinolin-3-one

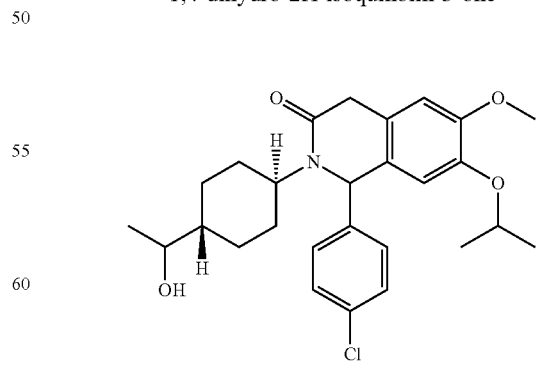

To a stirred solution of Intermediate 15.2 (0.714 g, 1.42 mmol) in AcOH (16 ml) was added H$_2$SO$_4$ 97% (0.108 ml, 1.99 mmol). The solution was stirred for 2.5 h at 100° C. The reaction mixture was concentrated in vacuo. The residue was extracted between 1M NaHCO₃ and EtOAc (2×). The organic phases were washed with brine and dried over Na₂SO₄, filtered and evaporated to dryness. The residue was dissolved in MeOH (16 ml) with stirring and potassium carbonate (0.590 g, 4.27 mmol) was added. Stirring was continued for 4 h at RT. The reaction mixture was concentrated in vacuo and the residue extracted between water and EtOAc (2×). The organic phases were washed with brine and dried over Na₂SO₄, filtered and evaporated to dryness. Purification of the residue by normal phase column chromatography, eluting with DCM-MeOH 95:5, gave the title compound as a slightly yellow foam (475 mg, 0.936 mmol, 65%). HPLC: $^A t_{Ret}$=5.59; LC-MS: m/z 472.4 [M+H]⁺.

Intermediate 15.2: 2-{2-[(4-Chloro-phenyl)-hydroxy-methyl]-4-isopropoxy-5-methoxy-phenyl}-N-[4-(1-hydroxy-ethyl)-cyclohexyl]-acetamide

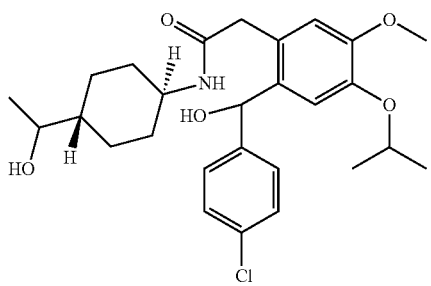 [SMILES: COc1cc(CC(=O)N[C@H]2CC[C@H](C(C)O)CC2)c(C(O)c2ccc(Cl)cc2)cc1OC(C)C]

The title intermediate (0.716 g, 1.428 mmol, 99%) was obtained as a slightly yellow foam from Intermediate 1.2 (0.500 g, 1.442 mmol) and Intermediate 15.3 (0.413 g, 2.88 mmol) analogously to Intermediate 2.2; HPLC: $^B t_{Ret}$=5.22 min; LC-MS: m/z 979.6 [2M+H]⁺;

Intermediate 15.3:
(trans)-1-(4-Amino-cyclohexyl)-ethanol

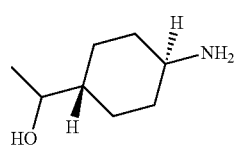

To the stirred solution of 4M HCl (dioxane) (36.1 ml, 144 mmol) was added Intermediate 15.4 (2.04 g, 7.22 mmol) at 0° C. The reaction mixture was stirred for 1 h at RT. The mixture was concentrated in vacuo. Purification of the residue by normal phase column chromatography, eluting with DCM-MeOH-ammonia aq. 30% (40:10:1), gave the title compound as a white solid (0.430 g, 2.97 mmol, 41%). TLC (DCM-MeOH-aq. ammonia 30% (40:10:1)) R$^f$=0.15

Intermediate 15.4: (trans)-[4-(1-Hydroxy-ethyl)-cyclohexyl]-carbamic acid tert-butyl ester

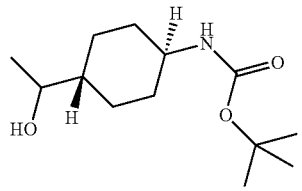 [SMILES: CC(O)[C@H]1CC[C@H](NC(=O)OC(C)(C)C)CC1]

To the stirred solution of (trans)-(4-formyl-cyclohexyl)-carbamic acid tert-butyl ester (4.55 g, 20 mmol) in THF (250 ml) was added methylmagnesium bromide (3M in diethyl ether) (6.67 ml, 20 mmol) during 2 min at −70° C. Stirring was continued for 20 min at −70° C. and then quenched with 1M NH₄Cl (200 ml). The mixture was extracted with TBME (2×). The organic phases were washed with brine and dried over Na₂SO₄, filtered and evaporated to dryness. Purification of the residue by normal phase column chromatography, eluting with EtOAc-heptane 1:1, gave the title compound after crystallization (diisopropyl ether-heptane) as a white solid (1.72 g, 7.0 mmol, 35%). TLC (EtOAc-heptane 1:1) R$^f$=0.37; ¹H NMR (600 MHz, DMSO-d₆): 0.86-1.81 (m, 9H), 0.99 (d, 3H), 1.36 (s, 9H), 3.09 (m, 1H), 3.32 (m, 1H), 4.27 (d, 1H), 6.67 (d, 1H)

Example 16

1-(4-Chloro-phenyl)-2-[4-(1-hydroxy-1-methyl-ethyl)-cyclohexyl]-7-isopropoxy-6-methoxy-1,4-dihydro-2H-isoquinolin-3-one

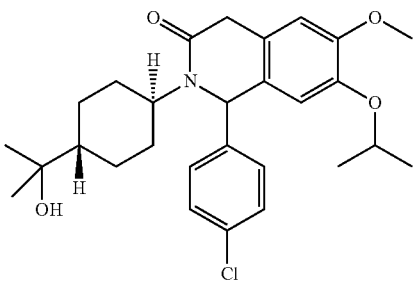 [SMILES: COc1cc2c(cc1OC(C)C)C(c1ccc(Cl)cc1)N([C@H]1CC[C@H](C(C)(C)O)CC1)C(=O)C2]

To the stirred solution of Example 15 (100 mg, 0.211 mmol) in THF (1.05 ml) was added methylmagnesium bromide (3M in diethyl ether) (0.126 ml, 0.329 mmol) during 2 min at −15° C. Stirring was continued for 2 h at RT and then quenched with 1M NH₄Cl. The mixture was extracted with EtOAc (2×). The organic phases were washed with brine and dried over Na₂SO₄, filtered and evaporated to dryness. The resulting crude material was purified by reverse phase prep- HPLC (Waters system) to yield the title compound as a beige foam (17 mg, 0.035 mmol, 17%). HPLC: $^B t_{Ret}$=5.71; LC-MS: m/z 486.3 [M+H]$^+$.

Example 17

1-(4-Chloro-phenyl)-2-{4-[hydroxy-(tetrahydro-pyran-4-yl)-methyl]-cyclohexyl}-7-isopropoxy-6-methoxy-1,4-dihydro-2H-isoquinolin-3-one

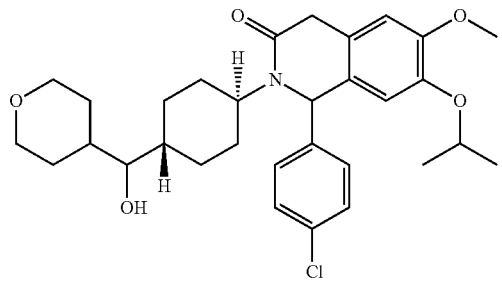 [SMILES: COc1cc2c(cc1OC(C)C)C(c1ccc(Cl)cc1)N([C@H]1CC[C@H](C(O)C3CCOCC3)CC1)C(=O)C2]

To the stirred solution of Intermediate 17.1 (1.20 g, 2.14 mmol) in AcOH (26 ml) was added H$_2$SO$_4$ 97% (0.160 ml, 3.0 mmol). The solution was stirred for 1 h at 100° C. The reaction mixture was concentrated in vacuo. The residue was extracted between 1M NaHCO$_3$ and EtOAc (2×). The organic phases were washed with brine and dried over Na$_2$SO$_4$, filtered and evaporated to dryness. The residue was dissolved in MeOH (26 ml) with stirring and potassium carbonate (0.888 g, 6.43 mmol) was added. The mixture was stirred for 4 h at 60° C. The reaction mixture was concentrated in vacuo and the residue extracted between water and EtOAc (2×). The organic phases were washed with brine and dried over Na$_2$SO$_4$, filtered and evaporated to dryness. Purification of the residue by normal phase column chromatography, eluting with DCM-MeOH 95:5, gave the title compound as a slightly yellow foam (0.634 g, 1.158 mmol, 54%). HPLC: $^B t_{Ret}$=5.60; LC-MS: m/z 542.3 [M+H]$^+$.

Intermediate 17.1: 2-{2-[(4-Chloro-phenyl)-hydroxy-methyl]-4-isopropoxy-5-methoxy-phenyl}-N-{4-[hydroxy-(tetrahydro-pyran-4-yl)-methyl]-cyclohexyl}-acetamide

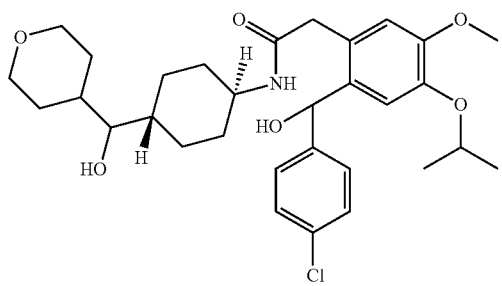 [SMILES: COc1cc(CC(=O)N[C@H]2CC[C@H](C(O)C3CCOCC3)CC2)c(C(O)c2ccc(Cl)cc2)cc1OC(C)C]

To the stirred mixture of Intermediate 1.2 (1.70 g, 4.90 mmol) and triethylamine (34 ml) was added Intermediate 17.2 (2.45 g, 9.80 mmol) and 2-hydroxy pyridine (0.466 g, 4.90 mmol). The mixture was stirred for 16 h at 80° C. The cooled reaction mixture was extracted between EtOAc (2×) and 1M aqueous NaHCO3 (1×). The organic phases were washed with brine and dried over Na$_2$SO$_4$, filtered and evaporated. Purification of the residue by normal phase column chromatography, eluting with DCM-MeOH 95:5, gave the title compound after crystallization (TBME) as a slightly yellow solid (1.87 g, 3.34 mmol, 68%). HPLC: $^B t_{Ret}$=5.22; LC-MS: m/z 1119.5 [2M+H]$^+$.

Intermediate 17.2: (trans)-(4-Amino-cyclohexyl)-(tetrahydro-pyran-4-yl)-methanol hydrochloride

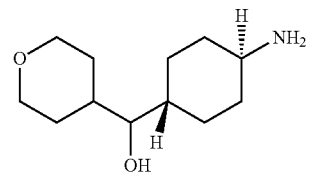 [SMILES: N[C@H]1CC[C@H](C(O)C2CCOCC2)CC1]

To the stirred solution of 4M HCl (dioxane) (50 ml, 200 mmol) was added Intermediate 17.3 (3.14 g, 10 mmol) at 0° C. The reaction mixture was stirred for 2 h at RT. The suspension was concentrated in vacuo and to the residue was added TBME (50 ml) with stirring. The solid was filtered off, washed with TBME and dried in vacuo, to give the title compound as a white solid (2.47 g, 9.89 mmol, 99%). $^1$H NMR (600 MHz, DMSO-d$_6$): 1.04-1.33 (m, 8H), 1.54-1.63 (m, 3H), 1.79 (m, 1H), 1.95 (m, 2H), 2.88 (m, 2H), 3.24 (m, 2H), 3.85 (m, 2H), 4.39 (bs, 1H), 7.97 (bs, 3H)

Intermediate 17.3: (trans)-{4-[Hydroxy-(tetrahydro-pyran-4-yl)-methyl]-cyclohexyl}-carbamic acid tert-butyl ester

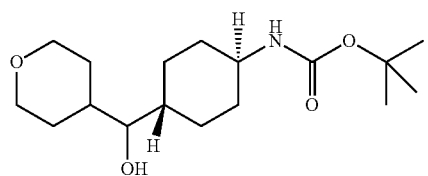 [SMILES: CC(C)(C)OC(=O)N[C@H]1CC[C@H](C(O)C2CCOCC2)CC1]

Reaction vessel 1:
To a solution of (trans)-(4-amino-cyclohexyl)-carbamic acid tert-butyl ester (11.37 g, 50.0 mmol) in THF (110 ml) (under argon atmosphere) was added trimethylchlorosilane (12.79 ml, 100 mol) at 0° C. The solution was stirred for 2 h at RT to get the "Aldehyde-TMSCl-Solution"
Reaction Vessel 2:
The stirred mixture of magnesium (Fluke 63035) (4.86 g, 200 mmol) and iodide (one crystal) in THF (50 ml) (under argon atmosphere) was heated to reflux temperature, then dropwise addition of a solution of 4-chlorotetrahydropyran (12.99 ml, 120 mmol), 1,2-dibromoethan (4.31 ml, 50 mmol) in THF (40 ml) during 30 min at this temperature (exothermic reaction). Stirring was continued for 30 min at reflux temperature. Then heating and stirring were stopped and the supernatant "Grignard-Solution" was transferred to Reaction vessel 3. To this "Grignard-Solution" was added the "Aldehyde-TMSCl-Solution" during 5 min at 35-40° C. Stirring was continued for 2 h at 30° C. and then quenched with 1M NH$_4$Cl (200 ml). The mixture was extracted with EtOAc (2×200 ml). The organic phases were washed with brine and dried over Na$_2$SO$_4$, filtered and evaporated to dryness. Purification of the residue by normal phase column chromatography, eluting with EtOAc-hexane 2:1, gave the title compound after crystallization (TBME) as a white solid (3.15 g, 10.05 mmol, 20%): TLC (EtOAc-heptane 2:1) $R_f$=0.19.

Example 18

1-(4-Chloro-phenyl)-7-isopropoxy-6-methoxy-2-[4-(tetrahydro-pyran-4-carbonyl)-cyclohexyl]-1,4-dihydro-2H-isoquinolin-3-one The title compound (0.444 g, 0.822 mmol, 71%) was obtained as a white foam from Example 17 (0.634 g, 1.158 mmol) analogously to Example 15; HPLC: $^B t_{Ret}$=5.78; LC-MS: m/z 540.3 [M+H]$^+$.

Example 19

(S)-1-(4-Chloro-phenyl)-7-isopropoxy-6-methoxy-2-[4-(tetrahydro-pyran-4-carbonyl)-cyclohexyl]-1,4-dihydro-2H-isoquinolin-3-one Example 20

(R)-1-(4-Chloro-phenyl)-7-isopropoxy-6-methoxy-2-[4-(tetrahydro-pyran-4-carbonyl)-cyclohexyl]-1,4-dihydro-2H-isoquinolin-3-one

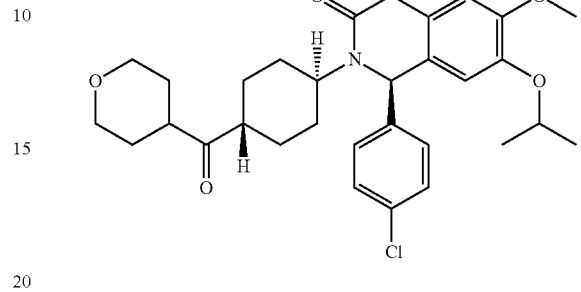

Preparative chiral separation of Example 18 (527 mg, 0.976 mmol): Column; Chiralpak AD-H 20 um, 50×500 mm; Mobile phase: Heptane-EtOH-MeOH 60:20:20; Flow: 90 ml/min Dedection: 235 nm (UV) afforded:

Example 19 first eluting peak ($R_t$=18.3 min) (250 mg, 0.458 mmol, 47%): HPLC: $^B t_{Ret}$=5.78; LC-MS: m/z 540.3 [M+H]$^+$.

Example 20 second eluting peak ($R_t$=33.4 min) (257 mg, 0.471 mmol, 48%): HPLC: $^B t_{Ret}$=5.78; LC-MS: m/z 540.3 [M+H]$^+$.

Example 21

1-(4-Chloro-phenyl)-2-{4-[1-hydroxy-1-(tetrahydro-pyran-4-yl)-ethyl]-cyclohexyl}-7-isopropoxy-6-methoxy-1,4-dihydro-2H-isoquinolin-3-one

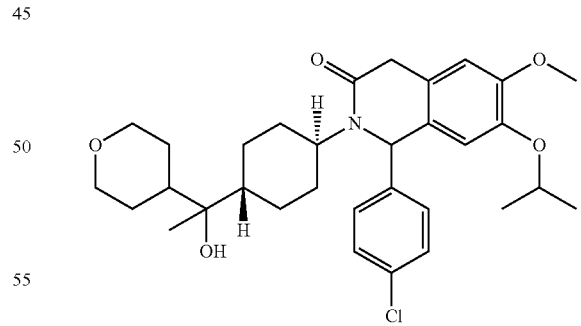

To the stirred solution of Example 18 (54 mg, 0.100 mmol) in THF (1 ml) was added methylmagnesium bromide (1.4M in toluene-THF 3:1) (0.20 ml, 0.28 mmol) during 2 min at 5° C. Stirring was continued for 2 h at 5° C. and then carefully quenched with 1M NH$_4$Cl. The mixture was extracted with EtOAc (2×). The organic phases were washed with brine and dried over Na$_2$SO$_4$, filtered and evaporated to dryness. Purification of the residue by normal phase column chromatography, eluting with DCM-MeOH 95:5, gave the title com-

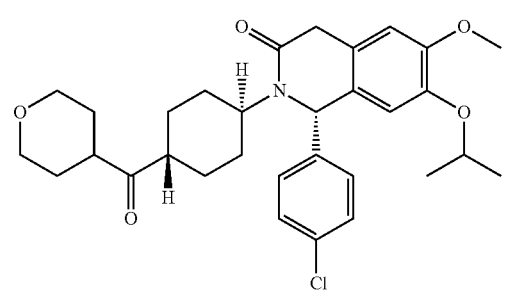 [SMILES: COc1cc2c(cc1OC(C)C)[C@H](c1ccc(Cl)cc1)N([C@H]1CC[C@H](C(=O)C3CCOCC3)CC1)C(=O)C2]

pound as a slightly yellow foam (35 mg, 0.060 mmol, 60%): HPLC: $^B t_{Ret}$=5.66/5.76; LC-MS: m/z 556.3 [M+H]$^+$.

Example 22

(S)-1-(4-Chloro-phenyl)-2-{4-[(R)-1-hydroxy-1-(tetrahydro-pyran-4-yl)-ethyl]-cyclohexyl}-7-isopropoxy-6-methoxy-1,4-dihydro-2H-isoquinolin-3-one

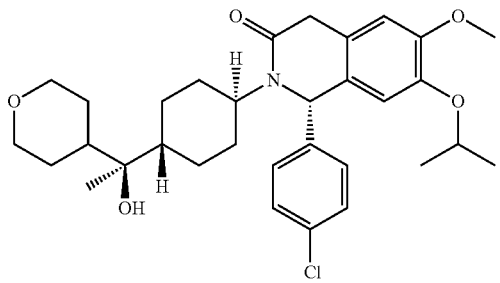

Example 23

(S)-1-(4-Chloro-phenyl)-2-{4-[(S)-1-hydroxy-1-(tetrahydro-pyran-4-yl)-ethyl]-cyclohexyl}-7-isopropoxy-6-methoxy-1,4-dihydro-2H-isoquinolin-3-one

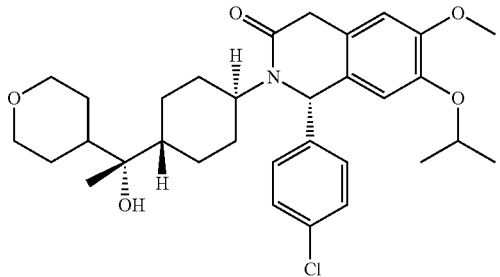 [SMILES: COc1cc2c(cc1OC(C)C)[C@H](c1ccc(Cl)cc1)N([C@H]1CC[C@H]([C@](C)(O)C3CCOCC3)CC1)C(=O)C2]

Preparative chiral separation of Intermediate 23.1 (72 mg, 0.129 mmol): Column; Chiralpak AD-H 20 um, 50×250 mm; Mobile phase: Heptane-EtOH 90:10; Flow: 12 ml/min Dedection: 220 nm (UV) afforded:

Example 22 first eluting peak (R$_t$=20.8 min) (27 mg, 0.046 mmol, 36%):
HPLC: $^B t_{Ret}$=5.61; LC-MS: m/z 556.4 [M+H]$^+$ Example 23 second eluting peak (R$_t$=30.3 min) (16 mg, 0.028 mmol, 22%):
HPLC: $^B t_{Ret}$=5.71; LC-MS: m/z 556.4 [M+H]$^+$.

Intermediate 23.1: (S)-1-(4-Chloro-phenyl)-2-{4-β-hydroxy-1-(tetrahydro-pyran-4-yl)-ethyl]-cyclohexyl}-7-isopropoxy-6-methoxy-1,4-dihydro-2H-isoquinolin-3-on

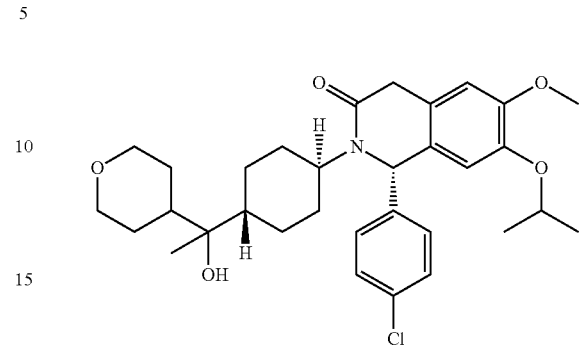

The title compound (0.073 g, 0.110 mmol, 24%) was obtained as a slightly yellow foam from Example 19 (0.245 g, 0.454 mmol) analogously to Example 21; HPLC: $^B t_{Ret}$=5.66/5.76; LC-MS: m/z 556.3 [M+H]$^+$.

Example 24

1-(4-Chloro-phenyl)-2-{4-[(3-fluoro-phenyl)-hydroxy-methyl]-cyclohexyl}-7-isopropoxy-6-methoxy-1,4-dihydro-2H-isoquinolin-3-one

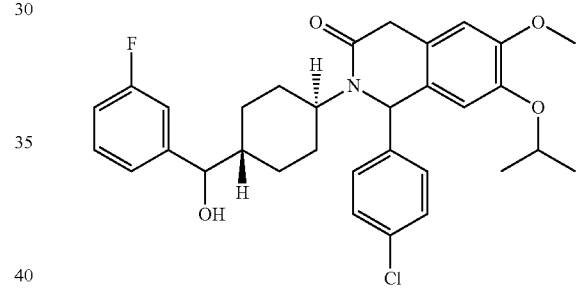

The title compound (0.460 g, 0.825 mmol) was obtained as a white foam starting with (trans)-(4-formyl-cyclohexyl)-carbamic acid tert-butyl ester and 3-fluorophenylmagnesium bromide (1M THF) analogously to Intermediates 15.4, 15.3, 15.2 and 15.1; HPLC: $^B t_{Ret}$=6.14/6.20; LC-MS: m/z 552.3 [M+H]$^+$.

Example 25

1-(4-Chloro-phenyl)-2-[4-(3-fluoro-benzoyl)-cyclohexyl]-7-isopropoxy-6-methoxy-1,4-dihydro-2H-isoquinolin-3-one

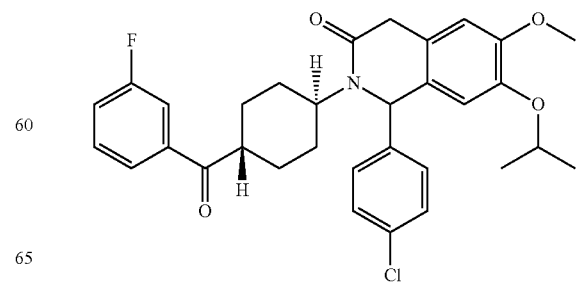

The title compound (0.200 g, 0.357 mmol, 46%) was obtained as a slightly yellow foam from Example 24 (0.424 g, 0.768 mmol) analogously to Example 15; HPLC: $^{B}t_{Ret}$=6.49; LC-MS: m/z 550.3 [M+H]$^{+}$.

Example 26

1-(4-Chloro-phenyl)-2-{4-[1-(3-fluoro-phenyl)-1-hydroxy-ethyl]-cyclohexyl}-7-isopropoxy-6-methoxy-1,4-dihydro-2H-isoquinolin-3-one

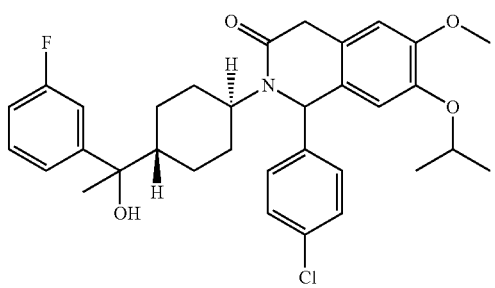 [SMILES: COc1cc2c(cc1OC(C)C)C(c1ccc(Cl)cc1)N([C@H]1CC[C@H](C(C)(O)c3cccc(F)c3)CC1)C(=O)C2]

The title compound (0.023 g, 0.040 mmol, 40%) was obtained as a white foam from Example 25 (0.055 g, 0.100 mmol) analogously to Example 21; HPLC: $^{B}t_{Ret}$=6.35; LC-MS: m/z 566.3 [M+H]$^{+}$.

Example 27

1-(4-Chloro-phenyl)-2-{4-[1-(3-fluoro-phenyl)-1-hydroxy-propyl]-cyclohexyl}-7-isopropoxy-6-methoxy-1,4-dihydro-2H-isoquinolin-3-one

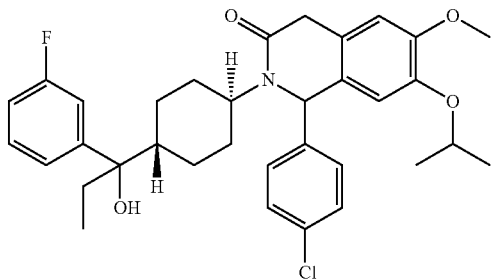 [SMILES: CCC(O)(c1cccc(F)c1)[C@H]1CC[C@H](N2C(=O)Cc3cc(OC)c(OC(C)C)cc3C2c2ccc(Cl)cc2)CC1]

The title compound (9.2 mg, 0.015 mmol, 15%) was obtained as a white foam from Example 25 (0.055 g, 0.100 mmol) analogously to Example 21 using ethylmagnesium bromide (1M THF); HPLC: $^{B}t_{Ret}$=6.63; LC-MS: m/z 580.3 [M+H]$^{+}$.

Example 28

1-(4-Chloro-phenyl)-2-[4-(1-hydroxy-1,3-dimethyl-butyl)-cyclohexyl]-7-isopropoxy-6-methoxy-1,4-dihydro-2H-isoquinolin-3-one

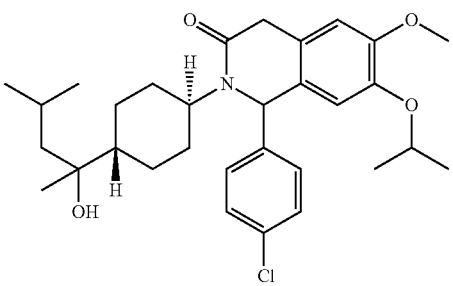 [SMILES: COc1cc2c(cc1OC(C)C)C(c1ccc(Cl)cc1)N([C@H]1CC[C@H](C(C)(O)CC(C)C)CC1)C(=O)C2]

To the stirred solution of Intermediate 28.1 (29 mg, 0.054 mmol) in THF (0.55 ml) was added trimethylchlorosilane (0.0069 ml, 0.054 mmol) at 0° C. After stirring an additional 30 min at 0° C., methylmagnesium bromide (1.4M in toluene-THF 3:1) (0.081 ml, 0.114 mmol) was added. Stirring was continued for 30 min at 0° C. and then carefully quench with 1M NH$_{4}$Cl. The mixture was extracted with EtOAc (2×). The organic phases were washed with brine and dried over Na$_{2}$SO$_{4}$, filtered and evaporated to dryness. Purification of the residue by normal phase column chromatography, eluting with EtOAc-heptane 3:1, gave the title compound as a white foam (18 mg, 0.034 mmol, 63%): HPLC: $^{B}t_{Ret}$=6.41/6.51; LC-MS: m/z 528.4 [M+H]$^{+}$. $^{1}$H NMR (600 MHz, DMSO-d$_{6}$): 0.85-1.84 (m, 27H), 3.37-3.60 (m, 2H), 3.66 (s, 3H), 3.78 (d, 1H), 4.29 (m, 1H), 4.48 (m, 1H), 5.87)s, 1H), 6.72 (s, 1H), 7.22 (s, 1H), 7.37 (dd, 4H)

Intermediate 28.1: 1-(4-Chloro-phenyl)-7-isopropoxy-6-methoxy-2-[4-(3-methyl-butyryl)-cyclohexyl]-1,4-dihydro-2H-isoquinolin-3-one

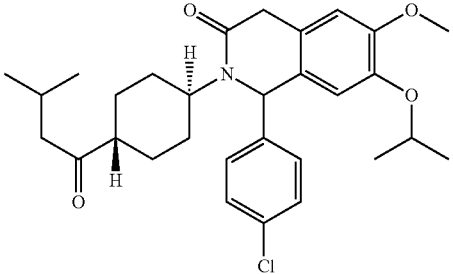 [SMILES: COc1cc2c(cc1OC(C)C)C(c1ccc(Cl)cc1)N([C@H]1CC[C@H](C(=O)CC(C)C)CC1)C(=O)C2]

The title compound (0.030 g, 0.056 mmol, 57%) was obtained as a slightly yellow foam from Example 28.2 (0.064 g, 0.099 mmol) analogously to Example 15; HPLC: $^B t_{Ret}$=6.46; LC-MS: m/z 512.4 [M+H]$^+$.

Intermediate 28.2: 1-(4-Chloro-phenyl)-2-[4-(1-hydroxy-3-methyl-butyl)-cyclohexyl]-7-isopropoxy-6-methoxy-1,4-dihydro-2H-isoquinolin-3-one

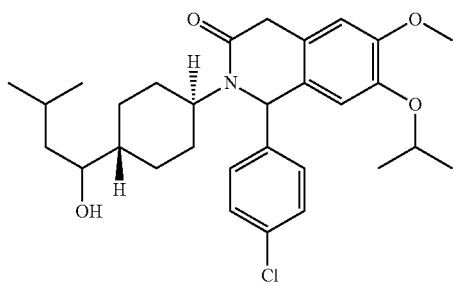 [SMILES: COc1cc2c(cc1OC(C)C)C(c1ccc(Cl)cc1)N([C@H]1CC[C@H](C(O)CC(C)C)CC1)C(=O)C2]

To the stirred solution of Intermediate 28.3 (94 mg, 0.202 mmol) in THF (2.0 ml) was added trimethylchlorosilane (0.026 ml, 0.202 mmol) at 0° C. After stirring an additional 30 min at 0° C., isobutylmagnesium chloride (2M THF) (0.222 ml, 0.444 mmol) was added. Stirring was continued for 60 min at 0° C. and then carefully quenched with 1M NH$_4$Cl. The mixture was extracted with EtOAc (2×). The organic phases were washed with brine and dried over Na$_2$SO$_4$, filtered and evaporated to dryness. Purification of the residue by normal phase column chromatography, eluting with DCM-MeOH 95:5, gave the title compound as a yellow foam (64 mg, 0.099 mmol, 49%): HPLC: $^B t_{Ret}$=6.30; LC-MS: m/z 514.3 [M+H]$^+$.

Intermediate 28.3: 4-[1-(4-Chloro-phenyl)-7-isopropoxy-6-methoxy-3-oxo-3,4-dihydro-1H-isoquinolin-2-yl]-cyclohexanecarbaldehyde

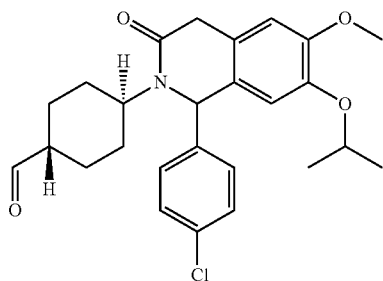 [SMILES: COc1cc2c(cc1OC(C)C)C(c1ccc(Cl)cc1)N([C@H]1CC[C@H](C=O)CC1)C(=O)C2]

To the stirred solution of Intermediate 28.4 (2.59 g, 5.66 mmol) in DMSO (28 ml) was added triethylamine (1.97 ml, 14.14 mmol). The mixture is cooled to 10° C. and sulfur trioxyde pyridine complex (2.25 g, 14.14 mmol) was added. The mixture was stirred for 1 h at 13-15° C. The reaction mixture was poured onto 1M citric acid (cold) and extracted with EtOAc (3×). The organic phases were washed with 1M citric acid (cold), water, 1M NaHCO$_3$, brine and dried over Na$_2$SO$_4$, filtered and evaporated. Purification of the residue by normal phase column chromatography, eluting with EtOAc-heptane 3:1, gave the title compound as white foam (1.69 g, 3.67 mmol, 65%): HPLC: $^B t_{Ret}$=5.55; LC-MS: m/z 456.2 [M+H]$^+$. $^1$H NMR (600 MHz, DMSO-d$_6$): 1.16-2.00 (m, 8H), 1.23-1.27 (q, 6H), 2.15 (m, 1H), 3.52 (dd, 2H), 3.68 (s, 3H), 4.28 (m, 1H), 4.49 (m, 1H), 5.88 (s, 1H), 6.75 (s, 1H), 7.20 (s, 1H), 7.39 (dd, 4H), 9.53 (s, 1H)

Intermediate 28.4: 1-(4-Chloro-phenyl)-2-(4-hydroxymethyl-cyclohexyl)-7-isopropoxy-6-methoxy-1,4-dihydro-2H-isoquinolin-3-one

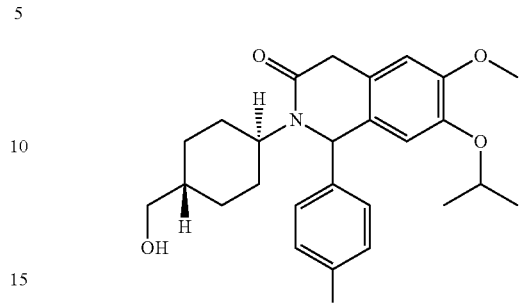

To a stirred solution of Intermediate 28.5 (2.29 g, 4.81 mmol) in AcOH (57 ml) was added H$_2$SO$_4$ 97% (0.366 ml, 6.74 mmol). The solution was stirred for 1.5 h at 100° C. The reaction mixture was concentrated in vacuo. The residue was extracted between 1M NaHCO$_3$ and EtOAc (2×). The organic phases were washed with brine and dried over Na$_2$SO$_4$, filtered and evaporated to dryness. The residue was dissolved in MeOH (57 ml) with stirring and potassium carbonate (1.995 g, 14.43 mmol) was added. The mixture was stirred for 1 h at 60° C. The reaction mixture was concentrated in vacuo and the residue extracted between water and EtOAc (2×). The organic phases were washed with brine and dried over Na$_2$SO$_4$, filtered and evaporated to dryness. Purification of the residue by normal phase column chromatography, eluting with DCM-MeOH 95:5, gave the title compound as a slightly yellow foam (1.54 g, 3.37 mmol, 70%). HPLC: $^A t_{Ret}$=5.31; LC-MS: m/z 458.2 [M+H]$^+$. $^1$H NMR (600 MHz, DMSO-d$_6$): 0.86-1.77 (m, 9H), 1.23-1.27 (q, 6H), 3.17 (t, 2H), 3.51 (dd, 2H), 3.68 (s, 3H), 4.31 (m, 1H), 4.40 (t, 1H), 4.50 (m, 1H), 5.88 (s, 1H), 6.75 (s, 1H), 7.23 (s, 1H), 7.39 (dd, 4H).

Intermediate 28.5: 2-{2-[(4-Chloro-phenyl)-hydroxy-methyl]-4-isopropoxy-5-methoxy-phenyl}-N-(4-hydroxymethyl-cyclohexyl)-acetamide

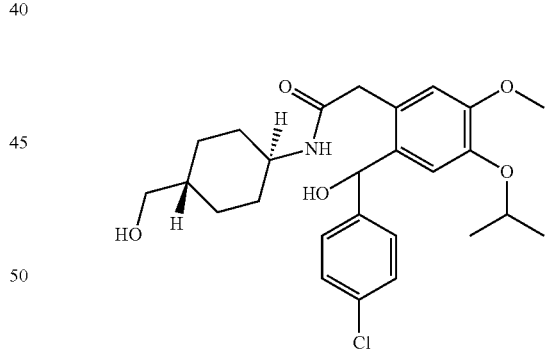

To a stirred mixture of Intermediate 1.2 (1.73 g, 5.00 mmol) in triethylamine (41.8 ml) was added (trans)-(4-amino-cyclohexyl)-methanol [CAS 1467-84-1] (0.807 g, 6.25 mmol) and 2-hydroxy pyridine (0.475 g, 5.00 mmol). The mixture was stirred for 4 h at 80° C. The cooled reaction mixture was extracted between EtOAc (2×) and 1M aqueous NaHCO3 (1×). The organic phases were washed with brine and dried over Na$_2$SO$_4$, filtered and evaporated. Purification of the residue by normal phase column chromatography, eluting with DCM-MeOH 95:5, gave the title compound as a white solid (2.30 g, 4.83 mmol, 97%). HPLC: $^B t_{Ret}$=4.99; LC-MS: m/z 951.5 [2M+H]$^+$.

Examples: 29, 30 and 31 were obtained analogously to Example 28 starting with Intermediate 28.3

| | Structure | Name/HPLC/MS |
|---|---|---|
| 29 | 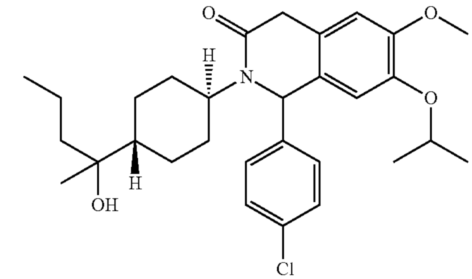 [SMILES: CCCC(C)(O)[C@H]1CC[C@H](N2C(=O)Cc3cc(OC)c(OC(C)C)cc3C2c2ccc(Cl)cc2)CC1] | 1-(4-Chloro-phenyl)-2-[4-(1-hydroxy-1-methyl-butyl)-cyclohexyl]-7-isopropoxy-6-methoxy-1,4-dihydro-2H-isoquinolin-3-one<br>HPLC: $^B t_{Ret}$ = 6.20/6.28; LC-MS: m/z 514.3 [M + H]$^+$. |
| 30 | 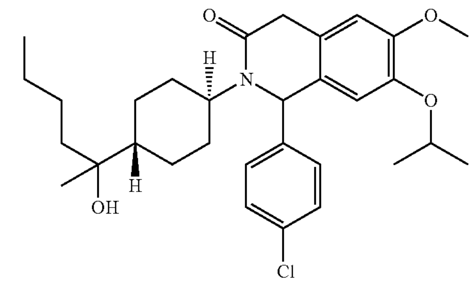 | 1-(4-Chloro-phenyl)-2-[4-(1-hydroxy-1-methyl-pentyl)-cyclohexyl]-7-isopropoxy-6-methoxy-1,4-dihydro-2H-isoquinolin-3-one<br>HPLC: $^B t_{Ret}$ = 6.44/6.53.; LC-MS: m/z 528.4 [M + H]$^+$. |
| 31 | 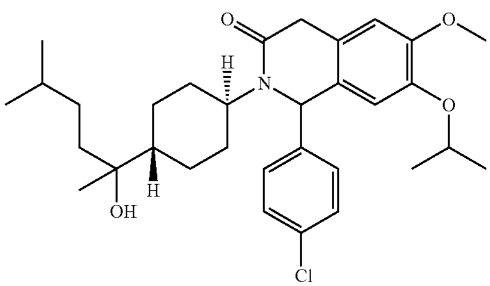 [SMILES: COc1cc2c(cc1OC(C)C)C(c1ccc(Cl)cc1)N([C@H]1CC[C@H](C(C)(O)CCC(C)C)CC1)C(=O)C2] | 1-(4-Chloro-phenyl)-2-[4-(1-hydroxy-1,4-dimethyl-pentyl)-cyclohexyl]-7-isopropoxy-6-methoxy-1,4-dihydro-2H-isoquinolin-3-one<br>HPLC: $^B t_{Ret}$ = 6.61/6.70; LC-MS: m/z 542.4 [M + H]$^+$. |

Example 32

1-(4-Chloro-phenyl)-2-[4-(1-furan-3-yl-1-hydroxy-ethyl)-cyclohexyl]-7-isopropoxy-6-methoxy-1,4-dihydro-2H-isoquinolin-3-one

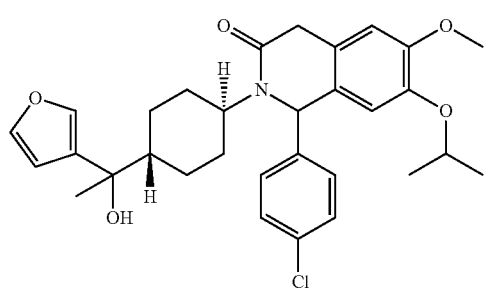 [SMILES: COc1cc2c(cc1OC(C)C)C(c1ccc(Cl)cc1)N([C@H]1CC[C@H](C(C)(O)c3ccoc3)CC1)C(=O)C2]

The title compound (0.023 g, 0.040 mmol) was obtained as a slightly yellow foam from Intermediate 32.1 (0.070 g, 0.122 mmol) analogously to Example 28 and Intermediate 28.1; HPLC: $^B t_{Ret}$=5.93; LC-MS: m/z 522.2 [M+H]$^+$.

Intermediate 32.1: 1-(4-Chloro-phenyl)-2-[4-(furan-3-yl-hydroxy-methyl)-cyclohexyl]-7-isopropoxy-6-methoxy-1,4-dihydro-2H-isoquinolin-3-one

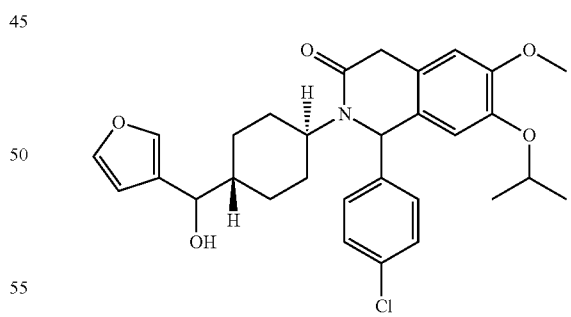

To a stirred solution of 3-bromo-furan (0.066 g, 0.439 mmol) in THF (1.0 ml) was added dropwise BuLi (1.6M in hexane) (0.287 ml, 0.459 mmol) during 10 min at −78° C. Stirring was continued for 10 min at −78° C. and then magnesiumbromide diethyletherate (0.113 g, 0.439 mmol) was added. Stirring was continued for 1 h at −78° C. The solution of Intermediate 28.3 (0.092 g, 0.200 mmol) in THF (0.5 ml) was added dropwise over 2 min at −78° C. Stirring was continued for 30 min at −78° C. and 1 h at 0° C., then carefully quenched with 1M NH₄Cl. The mixture was extracted with EtOAc (2×). The organic phases were washed with brine and dried over Na₂SO₄, filtered and evaporated to dryness. Purification of the residue by normal phase column chromatography, eluting with DCM-MeOH 95:5, gave the title compound as a yellow foam (72 mg, 0.126 mmol, 63%): HPLC: $^B t_{Ret}$=5.64/5.69; LC-MS: m/z 524.3 [M+H]⁺.

| | Mdm2 and Mdm4 inhibitory activity of representative compounds of the present invention: | |
|---|---|---|
| Example | IC₅₀ (µM) of p53-Hdm2 inhibition (TR-FRET) Assay | IC₅₀ (µM) of p53-Hdm4 inhibition (TR-FRET) Assay |
| 1 | 0.894 | 44.25 |
| 2 | 0.386 | nd |
| 3 | 0.183 | nd |
| 4 | 0.969 | 95.2 |
| 5 | 6.429 | nd |
| 6 | 4.408 | nd |
| 7 | 0.372 | 65.7 |
| 8 | 0.681 | 21.6 |
| 9 | 0.406 | 92.1 |
| 10 | 0.079 | 43.1 |
| 11 | 0.189 | nd |
| 12 | 0.257 | nd |
| 13 | 0.602 | 65.1 |
| 14 | 0.72 | 85.1 |
| 15 | 0.993 | 76.1 |
| 16 | 0.055 | 17.8 |
| 17 | 0.106 | 30.4 |
| 18 | 0.61 | 59.9 |
| 19 | 0.386 | 42.5 |
| 20 | 4.546 | 34.8 |
| 21 | 0.036 | 29.8 |
| 22 | 0.0125 | nd |
| 23 | 0.158 | nd |
| 24 | 0.072 | 48.9 |
| 25 | 0.531 | nd |
| 26 | 0.061 | nd |
| 27 | 0.266 | 63.4 |
| 28 | 0.0039 | nd |
| 29 | 0.0077 | nd |
| 30 | 0.0063 | 13.8 |
| 31 | 0.0070 | nd |
| 32 | 0.0276 | nd | nd = not determined.

The invention claimed is:
1. A compound of formula (I):

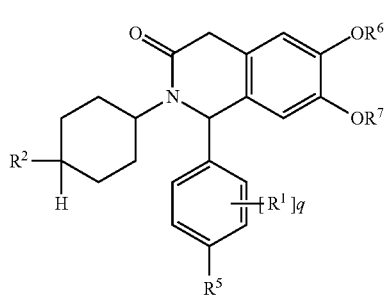

wherein
$R^1$ is halogen or cyano;
q is 0, 1 or 2;
$R^2$ is:
H,
$R^8(R^9)N$—,
$R^{10}$—C(O)—, or

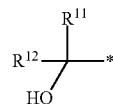

where * marks the point of attachment to the rest of the molecule
$R^5$ is halo or cyano;
$R^6$ is
(C₁-C₄)alkyl, wherein optionally one, several, or all of the hydrogen atoms are replaced with deuterium, and wherein said (C₁-C₄)alkyl is optionally substituted with 1, 2, 3 or 4 halo substituents, or
(C₁-C₄)alkoxy(C₁-C₄)alkyl-;
$R^7$ is (C₁-C₇)alkyl, wherein optionally one, several, or all of the hydrogen atoms are replaced with deuterium;
$R^8$ is
H,
(C₁-C₄)alkyl, wherein said (C₁-C₄)alkyl is optionally substituted with 1, 2 or 3 substituents independently selected from halo, cyano and OH,
(C₁-C₄)alkyl-C(O)—, wherein said (C₁-C₄)alkyl-C(O)— is optionally substituted with 1, 2 or 3 substituents independently selected from halo, cyano and OH,
$R^{13}(R^{14})N$—C(O)—(CH₂)ₙ—, or
HC(O)—;
$R^9$ is H, heterocyclyl², or (C₁-C₇)alkyl, said (C₁-C₇)alkyl being optionally substituted with 1, 2 or 3 substituents independently selected from halo, cyano and OH;
or $R^8$ and $R^9$ together with the nitrogen atom to which they are attached form heterocyclyl¹, said heterocyclyl¹ being optionally substituted by 1 or 2 substituents independently selected from (C₁-C₄)alkyl and =O;
heterocyclyl¹ is a 4, 5 or 6 membered saturated or partially unsaturated monocyclic ring, comprising ring carbon atoms and optionally 1 ring heteroatom independently selected from N, O and S in addition to the ring N atom to which $R^8$ and $R^9$ are attached;
$R^{10}$ is
H,
(C₁-C₆)alkyl, wherein said (C₁-C₆)alkyl is optionally substituted with 1, 2 or 3 substituents independently selected from halo, cyano and OH,
heterocyclyl²,
phenyl, said phenyl being optionally substituted with 1 or 2 substituents independently selected from halo, cyano, OH and (C₁-C₄)alkyl, said (C₁-C₄)alkyl being optionally substituted with 1, 2 or 3 halo substituents, or
heteroaryl², said heteroaryl² being optionally substituted with 1 or 2 substituents independently selected from halo and (C₁-C₄)alkyl, wherein said (C₁-C₄)alkyl is optionally substituted with 1, 2 or 3 substituents independently selected from halo, cyano and OH;
$R^{11}$ is
H,
(C₁-C₇)alkyl, wherein said (C₁-C₇)alkyl is optionally substituted with 1, 2 or 3 substituents independently selected from halo, cyano and OH,
heterocyclyl²,
phenyl, said phenyl being optionally substituted with 1 or 2 substituents independently selected from halo, cyano, OH and (C₁-C₄)alkyl, said (C₁-C₄)alkyl being optionally substituted with 1, 2 or 3 halo substituents, heteroaryl$^1$, said heteroaryl$^1$ being optionally substituted with 1 or 2 substituents independently selected from halo and (C$_1$-C$_4$)alkyl, wherein said (C$_1$-C$_4$)alkyl is optionally substituted with 1, 2 or 3 substituents independently selected from halo, cyano and OH, or R$^{13}$(R$^{14}$)N—C(O)—(CH$_2$)$_m$—;

m is 1 or 2;

heterocyclyl$^2$ is a 4, 5 or 6 membered saturated or partially saturated monocyclic group comprising ring carbon atoms and 1 or 2 ring heteroatoms independently selected from N, O and S;

heteroaryl$^1$ is a 5 or 6 membered fully unsaturated monocyclic group comprising ring carbon atoms and 1, 2, 3 or 4 ring heteroatoms independently selected from N, O and S, wherein the total number of ring S atoms does not exceed 1, and the total number of ring O atoms does not exceed 1;

heteroaryl$^2$ is a 5 membered fully unsaturated monocyclic group comprising ring carbon atoms and 1, 2, 3 or 4 ring heteroatoms independently selected from N, O and S, wherein the total number of ring S atoms does not exceed 1, and the total number of ring O atoms does not exceed 1;

R$^{12}$ is H, (C$_1$-C$_4$)alkyl, wherein said (C$_1$-C$_4$)alkyl is optionally substituted with 1, 2 or 3 substituents independently selected from halo, cyano and OH;

R$^{13}$ is H or (C$_1$-C$_4$)alkyl, wherein said (C$_1$-C$_4$)alkyl is optionally substituted with 1, 2 or 3 substituents independently selected from halo, cyano and OH;

R$^{14}$ is H or (C$_1$-C$_4$)alkyl, wherein said (C$_1$-C$_4$)alkyl is optionally substituted with from one to three substituents independently selected from halo, cyano and OH; and n is 0, 1, 2 or 3.

2. The compound of formula (I) or salt thereof as claimed in claim 1, wherein

R$^2$ is:

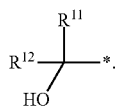

3. The compound of formula (I) or salt thereof as claimed in claim 1, wherein

R$^{12}$ is methyl and R$^{11}$ is (C$_1$-C$_5$)alkyl.

4. The compound of formula (I) or salt thereof as claimed in claim 1, wherein R$^2$ is CH$_3$—CH(CH$_3$)—CH$_2$—C(OH)(CH$_3$)—, CH$_3$CH$_2$CH$_2$—C(OH)(CH$_3$)—, CH$_3$CH$_2$CH$_2$CH$_2$—C(OH)(CH$_3$)—, or CH$_3$—CH(CH$_3$)—CH$_2$CH$_2$—C(OH)(CH$_3$)—.

5. The compound of formula (I) or salt thereof as claimed in claim 1, wherein R$^5$ is chloro.

6. The compound of formula (I) or salt thereof as claimed in claim 1, wherein R$^6$ methyl.

7. The compound of formula (I) or salt thereof as claimed in claim 1 wherein R$^7$ is isopropyl.

8. The compound of formula (I) or salt thereof as claimed in claim 1, wherein R$^8$ is (C$_1$-C$_4$)alkyl, wherein said (C$_1$-C$_4$)alkyl is optionally substituted with OH, (C$_1$-C$_4$)alkyl-C(O)—, wherein said (C$_1$-C$_4$)alkyl-C(O)— is optionally substituted with OH, R$^{13}$(R$^{14}$)N—C(O)—, or

HC(O)—.

9. The compound of formula (I) or salt thereof as claimed in claim 1, wherein R$^9$ is H, heterocyclyl$^2$ or (C$_1$-C$_4$)alkyl, said (C$_1$-C$_4$)alkyl being optionally substituted by OH.

10. The compound of formula (I) or salt thereof as claimed in claim 1, wherein R$^8$ and R$^9$ together with the nitrogen atom to which they are attached form heterocyclyl$^1$, said heterocyclyl$^1$ being optionally substituted by 1 =O substituent.

11. The compound of formula (I) or salt thereof as claimed in claim 1, wherein R$^{10}$ is H, (C$_1$-C$_4$)alkyl, heterocyclyl$^2$ or phenyl, said phenyl being optionally substituted with 1 or 2 halo substituents.

12. The compound of formula (I) or salt thereof as claimed in claim 1, wherein the stereochemistry of the compound of formula (I) is as shown in formula (Ia) below:

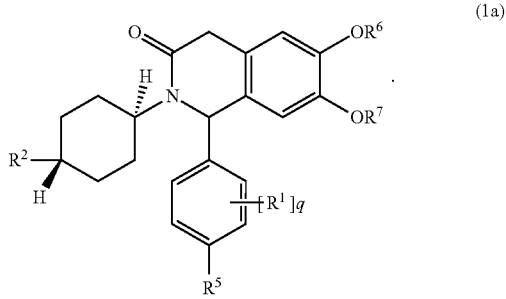

13. A pharmaceutical composition comprising a therapeutically effective amount of a compound of formula (I) or salt thereof as defined in claim 1, and one or more pharmaceutically acceptable carriers.

14. A method of modulating MDM2 and/or MDM4 activity in a subject, comprising the step of administering to a subject a therapeutically effective amount of a compound of formula (I) or salt thereof as defined in claim 1.

15. A compound of the formula (I) or salt thereof of claim 1, in combination with one or more therapeutically active agents.

* * * * *